US008100889B2

(12) United States Patent
Kawano et al.

(10) Patent No.: US 8,100,889 B2
(45) Date of Patent: Jan. 24, 2012

(54) BODY-INSERTABLE APPARATUS

(75) Inventors: Hironao Kawano, Tokyo (JP);
Hironobu Takizawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 247 days.

(21) Appl. No.: 11/658,969

(22) PCT Filed: Nov. 10, 2005

(86) PCT No.: PCT/JP2005/021067
§ 371 (c)(1),
(2), (4) Date: Jan. 30, 2007

(87) PCT Pub. No.: WO2006/052006
PCT Pub. Date: May 18, 2006

(65) Prior Publication Data
US 2009/0012503 A1    Jan. 8, 2009

(30) Foreign Application Priority Data

Nov. 10, 2004   (JP) ................................. 2004-326992
Nov. 11, 2004   (JP) ................................. 2004-327920

(51) Int. Cl.
 *A61K 9/22*    (2006.01)
(52) U.S. Cl. ..................... 604/891.1; 604/131; 604/153
(58) Field of Classification Search .................. 604/131, 604/132, 134, 135, 151–153, 891.1, 103.01, 604/892.1
See application file for complete search history.

(56) References Cited

U.S. PATENT DOCUMENTS

| | | | | |
|---|---|---|---|---|
| 3,692,027 A | * | 9/1972 | Ellinwood, Jr. ............ | 604/891.1 |
| 5,281,210 A | * | 1/1994 | Burke et al. ............... | 604/891.1 |
| 5,976,111 A | * | 11/1999 | Hart ............................... | 604/198 |
| 6,048,328 A | | 4/2000 | Haller et al. | |
| 6,312,409 B1 | * | 11/2001 | Gross ............................. | 604/131 |
| 6,416,495 B1 | | 7/2002 | Kriesel et al. | |
| 2004/0078028 A1 | * | 4/2004 | Flaherty et al. ............ | 604/892.1 |
| 2004/0115067 A1 | * | 6/2004 | Rush et al. .................... | 417/322 |
| 2004/0122348 A1 | * | 6/2004 | Hokanson et al. ................ | 604/9 |
| 2004/0204673 A1 | * | 10/2004 | Flaherty .......................... | 604/65 |

FOREIGN PATENT DOCUMENTS

| | | |
|---|---|---|
| JP | 55-030386 | 3/1980 |
| JP | 02-036848 | 2/1990 |
| JP | 04-138128 | 5/1992 |
| WO | WO 01/56633 A2 | 8/2001 |
| WO | WO 2005/030114 A1 | 4/2005 |

OTHER PUBLICATIONS

Japanese Office Action dated Oct. 5, 2010 with English translation.

* cited by examiner

*Primary Examiner* — Jackie Ho
*Assistant Examiner* — Emily Schmidt
(74) *Attorney, Agent, or Firm* — Scully, Scott, Murphy & Presser, P.C.

(57) ABSTRACT

A body-insertable apparatus is introduced in a subject to perform at least one of input and output of a predetermined fluid to and from the subject. The body-insertable apparatus includes a reservoir (2) in which the predetermined fluid is stored; a first communicating channel (4) whose one end is opened to an inside of the reservoir, the first communicating channel (4) being extended in a predetermined direction; a second communicating channel (5) whose one end is opened to an outside space of the body-insertable apparatus, the second communicating channel (5) being extended in a direction substantially parallel to the first communicating channel (4), and the second communicating channel (5) partially running parallel to the first communicating channel (4); and a control mechanism (6) which controls a communication state between the first communicating channel (4) and the second communicating channel (5).

20 Claims, 21 Drawing Sheets

BODY-INSERTABLE APPARATUS

TECHNICAL FIELD

The present invention relates to a body-insertable apparatus which is introduced in a subject to perform at least one of input and output of a predetermined fluid to and from the subject.

This application is based upon and claims the benefit of priority from Japanese Patent Application No. 2004-326992, filed Nov. 10, 2004 and Japanese Patent Application No. 2004-327920, filed Nov. 11, 2004, the entire contents of which are incorporated herein by reference.

BACKGROUND ART

Conventionally pieces of body-insertable apparatus which samples body fluid or the like of a patient (subject) have been proposed. Specifically the body-insertable apparatus has a configuration including a capsule-shaped external case, a reservoir which is arranged inside the external case to have a function of storing the body fluid or the like while communicated with the outside of the body-insertable apparatus, and an input control mechanism which controls input of the body fluid or the like to the reservoir. In the function of the body-insertable apparatus, at a stage in which the body-insertable apparatus reaches the subject such as the patient, the input control mechanism performs predetermined control to sample the body fluid or the like, and the sampled body fluid or the like is stored in the reservoir.

With reference to a specific example of the conventional body-insertable apparatus, the body-insertable apparatus including a predetermined control unit which is of an input control mechanism, a micro pump which is driven based on the control of the control unit, and a tank (reservoir) in which the fluid sampled based on the drive of the micro pump is stored has been proposed as described in Japanese Patent Application Laid-Open (JP-A) No. H4-138128. In the body-insertable apparatus, the micro pump is arranged in the path communicating the tank and a suction port opened to an outside space, and the fluid can be moved between the suction port and the reservoir to sample the fluid such as the body fluid of the subject by an action of the micro pump (for example, see JP-A No. H4-138128). Further, the body-insertable apparatus having a structure which includes a communication adjusting mechanism for adjusting a communication state between the reservoir and the suction port while the reservoir is configured to change an internal volume has also been proposed as another specific example.

The body-insertable apparatus which applies the above mechanism to directly supply a medicine to an affected part of the subject has also been proposed. For example, the body-insertable apparatus in which, while the medicine is previously stored in the tank, and the fluid is released by driving the micro pump in order to move the fluid from a discharge port to a suction port can be realized in the body-insertable apparatus described in JP-A No. H4-138128.

In order to create a suction force for sampling the body fluid and the like, a configuration in which a negative pressure is generated by rapidly changing the volume of the reservoir, for example, based on an action of a spring member is adopted in the conventional body-insertable apparatus. Specifically, for example, the conventional body-insertable apparatus is configured such that the reservoir and a piston are incorporated in a predetermined enclosure. The piston functions as a part of an outer wall portion (member defining an outer periphery of a region where storage subject is held) of the reservoir. While a snapping force is supplied by the predetermined spring member to the piston in a direction in which the volume of the reservoir is increased, a tension which cancels the snapping force is supplied to the piston by a predetermined fixed string. In this configuration, the piston included in the body-insertable apparatus is moved according to the snapping force supplied by the spring member when the fixed string is cut based on the action of the input control mechanism. Then, a negative pressure is generated in the reservoir to generated a suction force by increasing the volume of the reservoir according to the movement of the spring member, which allows the body fluid and the like of the subject to flow into the reservoir (for example, see JP-A No. H2-36848).

The body-insertable apparatus which applies the above mechanism to directly supply the medicine to the affected part and the like in the subject has also been proposed. The body-insertable apparatus adopts the structure in which the spring member supplies the snapping force in the direction in which the volume of the reservoir is decreased while the medicine is previously held in the reservoir. The snapping force of the spring member acts on the piston by cutting the fixed string based on the control of the input control mechanism, and the medicine held in the reservoir is released to the outside in association with the decrease in the reservoir volume.

DISCLOSURE OF INVENTION

However, in the conventional body-insertable apparatus, there is a problem that miniaturization is difficult. Generally, the body-insertable apparatus is operable by introducing the body-insertable apparatus in the subject such as the patient, and it is preferable to miniaturize as much as possible from the viewpoint of the decrease in load affecting the subject when used. On the other hand, in order to secure an amount of fluid sampled or released, the volume of the reservoir is required to some degree, and it is not easy to miniaturize the mechanism such as the micro pump. Accordingly, from the viewpoint of the miniaturization of the body-insertable apparatus, it is preferable to devise the configuration of a line communicating the reservoir and the outside space of the body-insertable apparatus. However, currently the conventional body-insertable apparatus in which such configuration has not been proposed yet.

Particularly, like the line communicating the discharge port and the reservoir and the suction port formed independently of the line in the example described in JP-A No. 4-138128, in the conventional body-insertable apparatus generally the line communicating the reservoir and the outside space is formed by the plural lines. In order to miniaturize the body-insertable apparatus including the plural lines, it is very important how the plural lines are arranged.

However, the conventional body-insertable apparatus (see JP-A No. H2-36848) has the problem that running cost is hardly reduced, because the conventional body-insertable apparatus has the configuration in which all the components such as the reservoir and the spring member are incorporated in the integrally formed enclosure. The problem will be described below.

When the body-insertable apparatus is used to release the medicine, it is necessary to prepare the pieces of body-insertable apparatus in which the plural kinds of the medicines are stored according to the purpose of use respectively. That is, because various medicines of which doses are given to the subject with the body-insertable apparatus are used according to the purpose, when the integrally formed body-insertable apparatus is used, it is necessary that the different pieces of body-insertable apparatus are previously prepared according to the kinds of the medicines. Accordingly, it is necessary that large storage space for keeping many pieces of body-insertable apparatus is secured while the many pieces of body-insertable apparatus in which the different medicines are stored are previously prepared, so that it is very difficult to reduce running costs.

In the conventional body-insertable apparatus, due to the difficulty of reuse, it is difficult to reduce running costs. Usually the conventional body-insertable apparatus adopts the configuration in which the reuse is not performed because of adhesion of the body fluid caused by the input and output of the fluid. However, with reference to the control mechanism, the structure in which the control mechanism is not in contact with the body fluid and the like can be realized when used. Accordingly, although the control mechanism can sufficiently be reused from a hygiene standpoint, since the conventional body-insertable apparatus adopts the configuration in which both the reservoir and the control mechanism are incorporated in the integrally formed enclosure, it is difficult to reuse the once-used body-insertable apparatus, which increases the running cost when compared with other reusable medical instruments.

Further, in the conventional body-insertable apparatus, from the viewpoint of short storage period, it is difficult to reduce the running cost. When the body-insertable apparatus is used to give the dose of the medicine or the like, the body-insertable apparatus is kept while the medicine is left in the reservoir. However, the optimum storage condition of the medicine stored in the reservoir does not always coincide with the optimum storage condition of the control mechanism. Specifically, when an electronic circuit such as a circuit for receiving a control signal supplied from the outside is used in order to control timing at which the fixed string is cut, sometimes the conditions such as temperature and humidity suitable for the storage of the electronic circuit differs from the conditions such as the temperature and the humidity suitable for the storage of the medicine. However, since the conventional body-insertable apparatus adopts the configuration in which both the reservoir and the control mechanism are included in the integrally formed enclosure, it is difficult that the storage condition is optimized. As a result, it is necessary to shorten the storage period, the amount of disposal of the unused body-insertable apparatus is increased, and the running cost is increased.

In view of the foregoing, an object of the invention is to realize a body-insertable apparatus which can be miniaturized by devising a configuration of a communicating channel between the reservoir and the outside space, and includes a predetermined reservoir to perform at least one of the release and the suction of fluid between the reservoir and the outside space.

Another object of the invention is to realize a structure in which running cost can be reduced, in the body-insertable apparatus introduced in the subject and in the body-insertable apparatus including the reservoir in which the fluid inputted to and/or outputted from the subject is stored and the control mechanism which performs timing control such as input.

A body-insertable apparatus which is introduced in a subject to perform at least one of input and output of a predetermined fluid to and from the subject, according to one aspect of the present invention, includes a reservoir in which the predetermined fluid is stored; a first communicating channel whose one end is opened to an inside of the reservoir, the first communicating channel being extended in a predetermined direction; a second communicating channel whose one end is opened to an outside space of the body-insertable apparatus, the second communicating channel being extended in a direction substantially parallel to the first communicating channel, and the second communicating channel partially running parallel to the first communicating channel; and a control mechanism which controls a communication state between the first communicating channel and the second communicating channel.

According to this aspect, since the first communicating channel and the second communicating channel are formed so as to be extended in the directions parallel to each other, a distance between the first communicating channel and the second communicating channel is not enlarged as the first communicating channel and the second communicating channel are extended. Therefore, occupied space regions of the first communicating channel, the second communicating channel, and the member constituting the first communicating channel and the second communicating channel can be decreased in the body-insertable apparatus, and the body-insertable apparatus can be miniaturized according to the decrease in occupied space region.

The body-insertable apparatus may further include a communication adjusting mechanism which adjusts the communication state between an opening formed at the other end of the first communicating channel and an opening formed at the other end of the second communicating channel. The control mechanism controls the communication state between the first communicating channel and the second communicating channel by controlling a drive state of the communication adjusting mechanism.

In the body-insertable apparatus, the first communicating channel and the second communicating channel may be formed by the same member.

In the body-insertable apparatus, the second communicating channel may be substantially formed on an central axis in a longitudinal direction of the body-insertable apparatus.

In the body-insertable apparatus, the reservoir, the first communicating channel, and the second communicating channel may form a reservoir unit. The control mechanism, the communication adjusting mechanism, and the reservoir unit may be sequentially arranged in the body-insertable apparatus.

In the body-insertable apparatus, the reservoir unit may be formed while being detachable from other regions in the body-insertable apparatus.

In the body-insertable apparatus, the predetermined fluid outputted from the subject may be previously stored in the reservoir, and the reservoir is formed such that a volume of a region in which the predetermined fluid is stored is changed according to the output of the predetermined fluid. The reservoir unit further may have an air space region whose volume is changed according to the volume change of the region, and the reservoir unit is formed such that the air space region and other space regions in the body-insertable apparatus are kept in a communicated state while the reservoir unit is mounted on the body-insertable apparatus.

The body-insertable apparatus may further include a weight member which is arranged near the opening of the second communicating channel. The opening of the second communicating channel is opened to the outside space of the body-insertable apparatus. The weight member acts so that the opening is opened downward in a vertical direction in the subject.

In the body-insertable apparatus, the body-insertable apparatus may be formed so that a center of gravity is located near the opening of the second communicating channel to the outside space of the body-insertable apparatus.

A body-insertable apparatus which is introduced in a subject to perform at least one of input and output of a predetermined fluid to and from the subject, according to another aspect of the present invention, includes a reservoir in which the predetermined fluid is stored; a first communicating channel in which one end is opened to an inside of the reservoir while the other end is opened at a predetermined position in the body-insertable apparatus; a second communicating channel in which one end is opened to an outside space of the body-insertable apparatus while the other end is opened near the opening in the other end of the first communicating channel; a communication adjusting mechanism which adjusts a communication state between the openings in the other end of the first communicating channel and in the other end of the second communicating channel; and a control mechanism which controls the communication state between the first communicating channel and the second communicating channel by the communication adjusting mechanism.

In the body-insertable apparatus, the opening at the other end of the first communicating channel and the opening at the other end of the second communicating channel may be formed on the substantially same plane.

In the body-insertable apparatus, the first communicating channel and the second communicating channel may be extended in directions parallel to each other near at least the other end of each of the first communicating channel and the second communicating channel. The communication adjusting mechanism may include a sheet member which is arranged such that the opening at the other end of each of the first communicating channel and the second communicating channel are covered with the sheet member. The control mechanism may control the communication state between the first communicating channel and the second communicating channel by applying a variable pressing force to the sheet member in a direction parallel to the direction in which the first communicating channel and the second communicating channel are extended near the other ends and in the direction in which the sheet member abuts onto at least one of the openings at the other end of the first communicating channel and at the other end of the second communicating channel.

In the body-insertable apparatus, the communication adjusting mechanism may further include a pressing member which generates the pressing force applied by the sheet member.

In the body-insertable apparatus, the first communicating channel and the second communicating channel may be formed near the other end of the first communicating channel and the other end of the second communicating channel so as to be extended at least in directions substantially parallel to a longitudinal axis of the body-insertable apparatus.

In the body-insertable apparatus, the communication adjusting mechanism may be a pump which moves the fluid from the other end of the first communicating channel to the other end of the second communicating channel.

In the body-insertable apparatus, a watertight member may be provided between the sheet member and the openings of at least one of the first communicating channel and the second communicating channel so as to surround the openings. The sheet member may control open and close of at least one of the first communicating channel and the second communicating channel.

In the body-insertable apparatus, the sheet member may be a coupling member which couples the opening at the other end of the first communicating channel and the opening at the other end of the second communicating channel.

In the body-insertable apparatus, the pressing member may be a shape-variable member whose shape is changed by one of a temperature change and electrical current passage.

In the body-insertable apparatus, the sheet member may be a shape-variable sheet whose shape is changed by one of the temperature change and the electrical current passage.

In the body-insertable apparatus, the pressing member may further include an elastic member which generates a pressing force. When the shape-variable member is driven, the shape-variable member may be deformed in the direction in which the pressing force generated by the elastic member is released.

Since the first communicating channel and the second communicating channel are formed so as to be extended in the directions parallel to each other, a distance between the first communicating channel and the second communicating channel is not enlarged as the first communicating channel and the second communicating channel are extended. Therefore, the body-insertable apparatus according to the invention has the effect that the occupied space regions of the first communicating channel, the second communicating channel, and the member constituting the first communicating channel and the second communicating channel can be decreased in the body-insertable apparatus and the effect that the body-insertable apparatus can be miniaturized according to the decrease in occupied space region.

Since the other end of the first communicating channel and the other end of the second communicating channel are formed so as to be opened in the same plane, and the communication adjusting mechanism adjusts the communication state between the other end of the first communicating channel and the other end of the second communicating channel. Therefore, the body-insertable apparatus according to the invention has the effect that the structure of the communication adjusting mechanism can be simplified and thereby the body-insertable apparatus can be miniaturized.

The body-insertable apparatus according to the invention is configured so that other components of the body-insertable apparatus are detachable from the reservoir unit. Therefore, from the standpoint that other components of the body-insertable apparatus can easily be reused, the body-insertable apparatus according to the invention has an effect that the running cost can be reduced.

BEST MODE(S) FOR CARRYING OUT THE INVENTION

Figure 1:
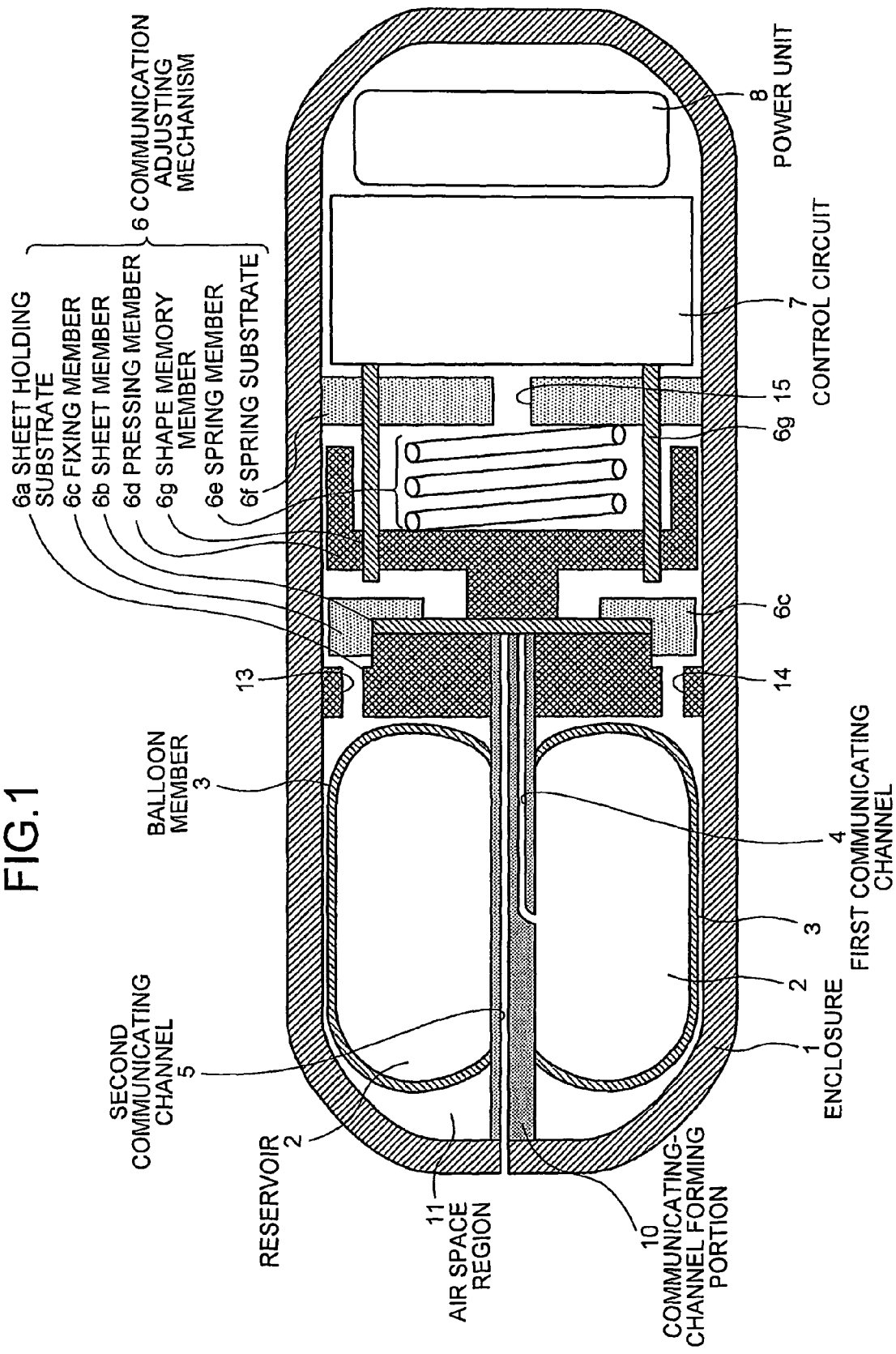
FIG. 1 is a sectional view schematically showing a configuration of a body-insertable apparatus according to a first embodiment.

Exemplary embodiments of a body-insertable apparatus according to the invention will be described below. It should be noted that all the drawings differ from the real drawings in a relationship between a thickness and a width in each portion, a thickness ratio of each potion, and the like because the drawing are schematic, and it is also obvious that the drawings differ from one another in the size relationship and the ratio.

First Embodiment

A body-insertable apparatus according to a first embodiment will first be described. The body-insertable apparatus according to the first embodiment is used in order to release the fluid such as the medicine previously stored in the reservoir to the outside space, i.e., a tissue inside the subject at a predetermined position inside the subject.

FIG. 1 is a schematic view showing an entire configuration of the body-insertable apparatus according to the first embodiment. As shown in FIG. 1, in the inside of an enclosure 1 defining an outer shape, the body-insertable apparatus according to the first embodiment includes a reservoir 2, a balloon member 3, a first communicating channel 4, and a second communicating channel 5. The medicine or the like which are of the released fluid are previously stored in the reservoir 2. The balloon member 3 forms a part of an outer wall portion of the reservoir 2, and the balloon member 3 changes a volume of the reservoir 2. The first communicating channel 4 and the second communicating channel 5 function as a passage when the reservoir 2 and the outside of the body-insertable apparatus are communicated with each other. The body-insertable apparatus according to the first embodiment also includes a communication adjusting mechanism 6, a control circuit 7, and a power unit 8. The communication adjusting mechanism 6 adjusts a communication state between the first communicating channel 4 and the second communicating channel 5. The control circuit 7 controls a drive state of the communication adjusting mechanism 6. The power unit 8 supplies drive electric-power to the control circuit 7.

The reservoir 2 is one in which the fluid such as the medicine outputted to the outside space of the body-insertable apparatus according to the first embodiment is previously stored. Specifically, in the first embodiment, the reservoir 2 is formed in a region which is covered with an inner surface of the balloon member 3 and a surface of a communicating channel forming portion 10, and the fluid is stored in the region. The balloon member 3 which forms almost all the outer wall portions of the reservoir 2 is made of an elastic material such as rubber. When the predetermined amount of fluid is injected, the balloon member 3 is kept in the state in which a membrane portion made of the elastic material is previously expanded. When the reservoir 2 and the outside space are communicated with each other by the later-mentioned action of the communication adjusting mechanism 6, the volume of the reservoir 2 is decreased to release the fluid to the outside space according to a contraction action of the membrane member.

The first communicating channel 4 and the second communicating channel 5 have the function of communicating the outside of the body-insertable apparatus according to the first embodiment (hereinafter simply referred to as "outside space") and the reservoir 2. The first communicating channel 4 and the second communicating channel 5 are formed in the communicating channel forming portion 10 so as to be extended in a direction parallel to a longitudinal direction of the body-insertable apparatus respectively. The communicating channel forming portion 10 has a rod-shaped structure extended along a central axis in the longitudinal direction of the body-insertable apparatus according to the first embodiment. With reference to at least the second communicating channel 5, the second communicating channel 5 is formed so as to be substantially located at the central axis with respect to the longitudinal direction of the body-insertable apparatus. In the more specific structure, one end of the first communicating channel 4 is opened toward an inner space of the balloon member 3, one end of the second communicating channel 5 is opened toward the outside space, the other end of the first communicating channel 4 and the other end of the second communicating channel 5 are opened on to the surface of a later-mentioned sheet holding substrate 6a, and the communication adjusting mechanism 6 adjusts the communication state between the opening formed at the other end of the first communicating channel 4 and the opening formed at the other end of the second communicating channel 5. The term "parallel" shall include not only the case where the first communicating channel 4 and the second communicating channel 5 are linearly extended and geometrically parallel, but also the case the central axes of the space regions forming the first communicating channel 4 and the second communicating channel 5 are parallel to each other even if the first communicating channel 4 and the second communicating channel 5 have the slightly curved shape.

The communication adjusting mechanism 6 is one which adjusts the communication state between the first communicating channel 4 and the second communicating channel 5 according to control of the control circuit 7. The communication adjusting mechanism 6 has the function of controlling the expansion and contraction action of the balloon member 3 which is of a flow generation portion by the adjustment action. Specifically the communication adjusting mechanism 6 includes the sheet holding substrate 6a, a sheet member 6b, and a fixing member 6c. A cross-sectional recess region is formed in the sheet holding substrate 6a. The sheet member 6b is arranged on the sheet holding substrate 6a such that the recess region is covered with the sheet member 6b. The fixing member 6c fixes an outer peripheral portion of the sheet member 6b to the sheet holding substrate 6a while the outer peripheral portion is in close contact with the sheet holding substrate 6a. The communication adjusting mechanism 6 also includes a pressing member 6d, a spring member 6e, a spring substrate 6f, and a shape memory member (shape-variable member) 6g. The pressing member 6d applies a predetermined pressing force to the sheet member 6b. The spring member 6e generates the pressing force applied by the pressing member 6d. The spring substrate 6f holds the spring member 6e. The shape memory member 6g changes a position of the pressing member 6d with respect to the sheet member 6b.

The sheet holding substrate 6a is formed by a plate body which holds the sheet member 6b. In the first embodiment, an end portion of the sheet holding substrate 6a is arranged while being in contact with an inside surface in a cylindrical portion of the enclosure 1. Therefore, the first embodiment has the structure in which vents 13 and 14 are formed such that an air space region 11 surrounded by the outside surface of the balloon member 3, the inner surface of the enclosure 1, and a backside of (face opposing to the face in which the sheet member 6b is arranged) the sheet holding substrate 6a is not shielded from other spaces. A vent 15 is formed in the spring substrate 6f base on the same reason.

The sheet member 6b is one which directly controls the communication state between the first communicating channel 4 and the second communicating channel 5. Specifically, for example, the sheet member 6b is made of the watertight and flexible material such as a silicone sheet, the sheet member 6b is arranged on the sheet holding substrate 6a such that the recess region formed in the sheet holding substrate 6a is covered with the sheet member 6b, and the outer peripheral portion of the sheet member 6b is fixed by the fixing member 6c while being in close contact with the sheet holding substrate 6a. When the pressing member 6d applies the predetermined pressing force, the sheet member 6b is kept in the state in which the sheet member 6b is in close contact with the end portion of the second communicating channel 5. Therefore, the sheet member 6b has the function of closing the opening of the second communicating channel 5 to block the communication state between the first communicating channel 4 and the second communicating channel 5. On the other hand, when the pressing force by the pressing member 6d is decreased, as described later, the sheet member 6b is separated from the end portion of the second communicating channel 5 by the change in shape, and the first communicating channel 4 and the second communicating channel 5 are communicated with each other.

The fixing member 6c is one which fixes the sheet member 6b to the sheet holding substrate 6a. Specifically the fixing member 6c has the function of fixing the outer peripheral portion of the sheet member 6b to the sheet holding substrate 6a in a close contact manner by applying the pressing force to the outer peripheral portion of the sheet member 6b toward the sheet holding substrate 6a side. When the fixing member 6c fixes the sheet member 6b in the above-described manner, in the central portion of the sheet member 6b (in FIG. 1, the region near the central axis in the longitudinal direction of the body-insertable system, more specifically the region corresponding to the position of the opening of the second communicating channel 5), while the shape is freely changed according to the pressing force of the pressing member 6d, the fluid (later described) flowing into the recess region of the sheet holding substrate 6a through the first communicating channel 4 is prevented from leaking to the region other than the second communicating channel 5.

The spring member 6e is one which generates the pressing force applied to the sheet member 6b by the pressing member 6d. Specifically, in the spring member 6e, one end is fixed to the spring substrate 6f while the other end is fixed to the pressing member 6d, and a spring length is kept shorter than a natural length. Therefore, the spring member 6e has the function of biasing a snapping force to the pressing member 6d toward the direction in which the sheet member 6b is located (leftward direction in FIG. 1).

The shape memory member 6g is one which changes the position of the pressing member 6d with respect to the sheet member 6b. Specifically the shape memory member 6g has the rod-shaped or coil-shaped structure in which one end is fixed to the spring substrate 6f while the other end is fixed to the pressing member 6d, and the shape memory member 6g is made of a shape memory alloy which has a predetermined electric resistance value while having predetermined shape memory properties. More specifically the shape memory member 6g has an enough length to cause the pressing member 6d to abut onto the sheet member 6b, e.g., under the temperature condition equal to the temperature inside the subject. On the other hand, the shape memory member 6g has the function in which the shape thereof is changed to separate the pressing member 6d from the sheet member 6b under the temperature condition that is sufficiently higher than a predetermined temperature, e.g., the temperature inside the subject.

The control circuit 7 is one which has the function of controlling the drive of the balloon member 3 which is of flow generating means through the presence or absence of electric current supply to the shape memory member 6g, and the control circuit 7 is one which functions as an example of control means in the invention. Specifically the control circuit 7 has the function of supplying the current to the shape memory member 6g when the body-insertable apparatus according to the first embodiment is introduced into the subject to reach a predetermined position of the subject. Joule heat is generated in the shape memory member 6g by the passage of the current through the shape memory member 6g, and the temperature of the shape memory member 6g is increased due to the Joule heat, which allows the shape of the shape memory member 6g to be changed. For example, a timer mechanism may be included as a configuration which defines current supply timing, or a control signal may be supplied from the outside while a wireless receiving mechanism is incorporated.

Then, an action of the body-insertable apparatus according to the first embodiment will be described. As described above, FIG. 2 is a schematic view for explaining the action of the body-insertable apparatus according to the first embodiment. The action will be described below with reference to FIG. 2.

Figure 2:
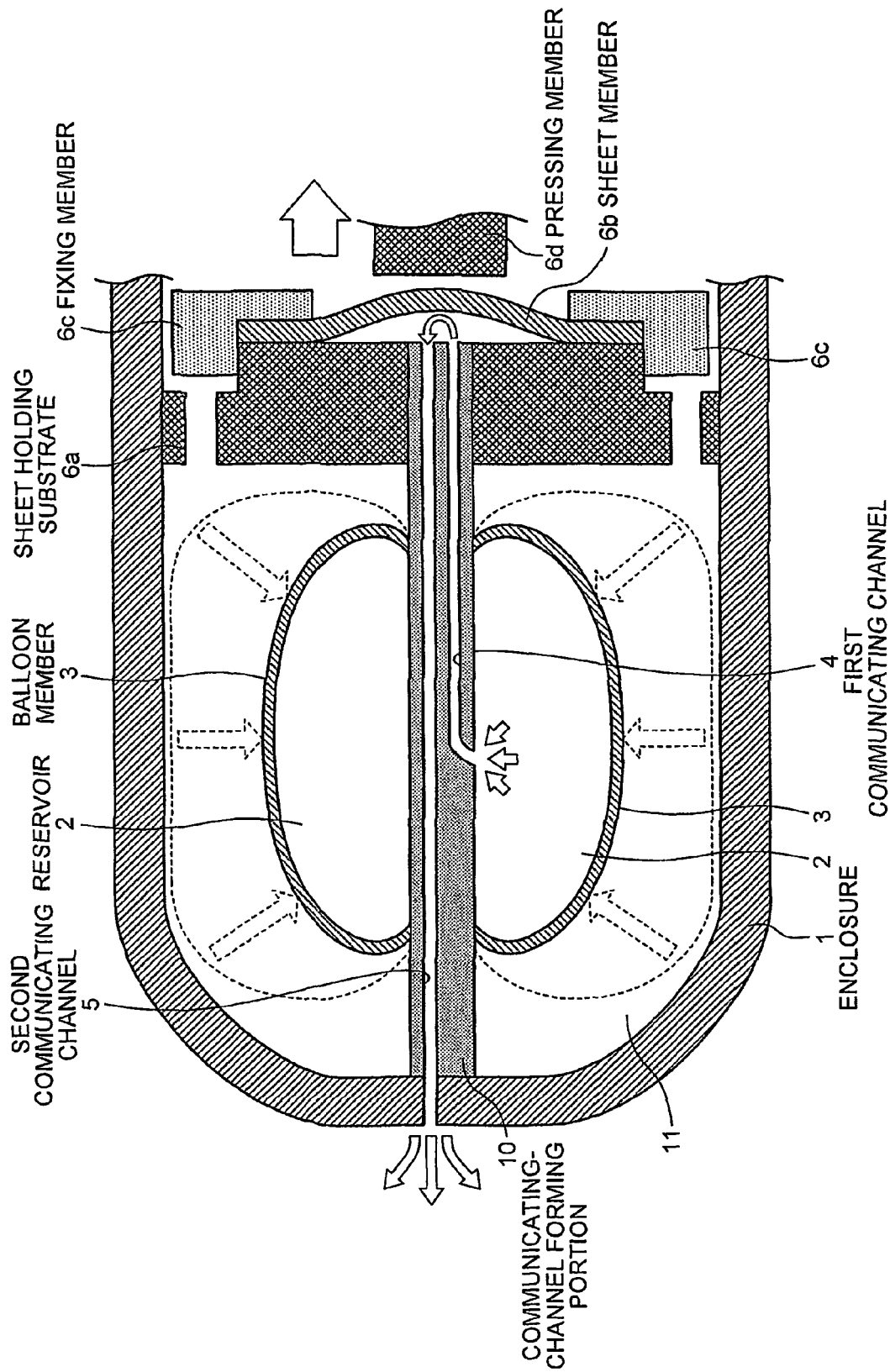
FIG. 2 is a schematic view for explaining an action of the body-insertable apparatus according to the first embodiment.

The control circuit 7 supplies the predetermined current to the shape memory member 6g, the temperature of the shape memory member 6g is raised due to the Joule heat generated according to the current, and the shape is changed. Specifically, the shape memory member 6g is previously formed such that the length in the longitudinal direction contracts during the high temperature, while the shape memory member 6g is formed in the rod shape. Therefore, the shape of the shape memory member 6g is changed such that the length in the longitudinal direction is shortened according to the temperature rise generated by the Joule heat. The pressing member 6d fixed to one end of the shape memory member 6g is moved toward the direction (rightward direction in FIG. 2) in which the pressing member 6d is separated from the sheet member 6b as shown in FIG. 2 according to the contraction of the length in the longitudinal direction of the shape memory member 6g, and the pressing force against the sheet member 6b is decreased or eliminated.

When the pressing force against the sheet member 6b is decreased, the close contact state between the sheet member 6b and the second communicating channel 5 is released, and the end portion of the first communicating channel 4 and the end portion of the second communicating channel 5 are communicated through the recess region formed in the sheet holding substrate 6a. As described above, the first communicating channel 4 is formed so as to be communicated with the inside space of the balloon member 3, and the second communicating channel 5 is formed so as to be communicated with the outside space of the body-insertable apparatus. Therefore, the first communicating channel 4 and the second communicating channel 5 are communicated with each other, which allows the inside space of the balloon member 3 and the outside space of the body-insertable apparatus to be communicated.

The contraction action of the expanding and contracting film forming the balloon member 3 is started by communicating the inside space of the balloon member 3 and the outside space of the body-insertable apparatus. Specifically, the volume of the reservoir 2 in which the reservoir 2 is substantially covered with the inner surface of the balloon member 3 is decreased by the contraction of the balloon member 3, as shown in FIG. 2 the fluid previously stored in the reservoir 2 flows into the first communicating channel 4, and the fluid is released into the outside space through a gap portion generated between the sheet holding substrate 6a and the sheet member 6b and through the second communicating channel 5. Thus, the output action of the fluid is performed by the body-insertable apparatus according to the first embodiment.

In the body-insertable apparatus according to the first embodiment, during the output action of the fluid, the volume of the air space region 11 is increased according to the decrease in volume of the reservoir 2. Therefore, the configuration in which the fluid flows into the air space region 11 from other space regions inside the enclosure 1 through the vents 13 and 14 is adopted in the first embodiment, and the generation of a negative pressure is suppressed in the air space region 11 to prevent the interruption of the contraction of the balloon member 3.

Then advantages of the body-insertable apparatus according to the first embodiment will be described. In the first embodiment, the first communicating channel 4 opened toward the reservoir 2 and the second communicating channel 5 opened toward the outside space are formed so as to be extended in the directions parallel to each other. The adoption of the above structure enables the body-insertable apparatus to be miniaturized in the first embodiment. Specifically, the first communicating channel 4 and the second communicating channel 5 are configured to be extended in the directions parallel to each other, which allows an occupied region of the communicating channel forming portion 10 to be decreased in the body-insertable apparatus. That is, when the first communicating channel and the second communicating channel are formed so as not to be parallel to each other, a distance between the first communicating channel and the second communicating channel is enlarged as the first communicating channel and the second communicating channel are extended, and the volume of the communicating channel forming portion in which the first communicating channel and the second communicating channel are formed is increased according to the enlargement of the distance. Therefore, in the body-insertable apparatus, the occupied regions of the first communicating channel, the second communicating channel, and the communicating channel forming portion in which the first communicating channel and the second communicating channel are formed are increased, which leads to requiring the increase in body-insertable apparatus in size.

For example, in the body-insertable apparatus described in JP-A No. 4-138128, the central axis direction of a suction port and the central axis direction of the line from a discharge port to a tank are formed so as to be perpendicular to each other. In the body-insertable apparatus having such the structure, because the communicating channel has the structure which is two-dimensionally extended as a whole, it is necessary to form the structure in which the members for forming the communicating channel (Si substrates 21 and 22 in JP-A No. 4-138128) are two-dimensionally enlarged in the two-dimensional direction including the two directions in which the lines are extended. Particularly, from the viewpoints of stabilization of an attitude of the body-insertable apparatus inside the subject and the like, actually it is preferable that the component such as a micro pump is arranged near the central axis in the longitudinal direction of the body-insertable apparatus. In the case where this structure is adopted, because it is necessary that the suction port is formed while extended by the predetermined length, the occupied regions of the communicating channel and the communicating channel forming portion are further increased.

On the contrary, in the body-insertable apparatus according to the first embodiment, the first communicating channel 4 and the second communicating channel 5 are formed so as to be substantially parallel to each other. Accordingly, the distance between the first communicating channel 4 and the second communicating channel 5 becomes substantially constant, the occupied regions of the first communicating channel 4, the second communicating channel 5, and the communicating channel forming portion 10 in which the first communicating channel 4 and the second communicating channel 5 are formed can be set to the minimum according to need, and the miniaturization of the body-insertable apparatus can be realized.

In the first embodiment, the first communicating channel 4 and the second communicating channel 5 have the linearly extended structure respectively, so that the first communicating channel 4 and the second communicating channel 5 has an advantage that the linearly extended structure enables the fluid to be smoothly released. That is, because sometimes the fluid stored in the reservoir 2 has viscosity to a certain extent, when the fluid is released into the outside space through the complicatedly curved communicating channel in such the case, there is a possibility of accumulation of the fluid or the generation of a vortex on the way to the communicating channel. In the first embodiment, the generation of a phenomenon in which the movement of the fluid is interrupted can be suppressed to smoothly release the fluid into the outside space by linearly forming the first communicating channel 4 and the second communicating channel 5.

The linear formation of the first communicating channel 4 and the second communicating channel 5 is of benefit from the viewpoint of the miniaturization of the body-insertable apparatus. That is, when the complicatedly curved communicating channel is provided, similarly to the case in which the extended direction of the first communicating channel and the extended direction of the second communicating channel are formed so as not to be parallel to each other, the occupied region of the communicating channel forming portion is increased. From such the viewpoint, the body-insertable apparatus can further be miniaturized by having the structure in which the first communicating channel 4 and the second communicating channel 5 are linearly extended.

In the body-insertable apparatus according to the first embodiment, one end portion of the first communicating channel 4 and one end portion of the second communicating channel 5 are formed so as to be opened in the same surface (surface of the sheet holding substrate 6a), and the body-insertable apparatus has the configuration in which the fluid is released by the control of the communication state between the openings in the same surface. In the first embodiment, the adoption of this configuration enables the structure of the communication adjusting mechanism 6 to be simplified. As a result of the simplification, the first embodiment has the advantage that the body-insertable apparatus can be miniaturized.

When the body-insertable apparatus is formed by using the first communicating channel 4 and the second communicating channel 5, during the time in which the fluid is not released, it is preferable to block the communication state between the first communicating channel 4 and the second communicating channel 5 from the viewpoints of leak prevention of the fluid stored in the reservoir 2 and the flow-in prevention of the fluid from the outside space. However, in the case of the adoption of the configuration in which the communication state is adjusted with the independent members with respect to the communicating channel, it is not appropriate, because the structure of the communication adjusting mechanism is complicated, and the body-insertable apparatus is enlarged. On the other hand, in the first embodiment, the communication state can easily be adjusted with the same member by adopting the above structure. That is, in the example shown in FIG. 1, both the communication state of the first communicating channel 4 and the communication state of the second communicating channel 5 can be adjusted by the single sheet member 6b which is arranged such that the openings at the end portions of the first communicating channel 4 and the second communicating channel 5 are covered with the sheet member 6b, the structure of the communication adjusting mechanism can be simplified. Therefore, the first embodiment has the advantage that the body-insertable apparatus can be miniaturized by simplifying the structure of the communication adjusting mechanism.

In the body-insertable apparatus according to the first embodiment, the first communicating channel 4 and the second communicating channel 5 are formed such that flow directions of the fluids become parallel (including the cases in which an angle formed by direction vectors is 0° and 180°) by causing the first communicating channel 4 and the second communicating channel 5 to become parallel to each other near the end portions opened in the surface of the sheet holding substrate 6a, and the communication adjusting mechanism 6 has the structure which applies the pressing force in the direction parallel to the flow direction. That is, the communication adjusting mechanism 6 can substantially cancel an outflow pressure by applying the pressing force substantially parallel to and opposite to the outflow pressure from the end portions of the first communicating channel 4 and the second communicating channel 5 to the communication adjusting mechanism 6 side, and the fluid leak from the first communicating channel 4 and the like can be prevented more efficiently.

The body-insertable apparatus according to the first embodiment has the structure in which both the first communicating channel 4 and the second communicating channel 5 are formed in the same communicating channel forming portion 10. In the first embodiment, the adoption of this structure enables the occupied space region of the communicating channel forming portion to be decreased in the body-insertable apparatus, and the body-insertable apparatus can be miniaturized.

When the first communicating channel 4 and the second communicating channel 5 are formed by the individual members, the two communicating channel forming portions are required. On the other hand, when the first communicating channel 4 and the second communicating channel 5 are formed by the same member, only the single communicating channel forming portion 10 can be arranged in the body-insertable apparatus. Particularly, in the communicating channel forming portion, it is necessary that a thickness except for the cavity portions (portion where lines are formed) is maintained to a certain extent in order to maintain predetermined physical strength. When the lines are formed by the individual members, the member having the above thickness is required for each of the plural communicating channel forming portions. Therefore, when compared with the case in which the lines are formed in the individual members, the use of the single communicating channel forming portion 10 enables the occupied space region of the communicating channel forming portion to be substantially decreased to a half.

In the first embodiment, the first communicating channel 4 and the second communicating channel 5 are formed so as to be extended toward the direction parallel to the longitudinal direction of the body-insertable apparatus at least near the sheet member 6b, so that an outer diameter about the central axis of the longitudinal direction can be prevented from increasing. That is, according to the adoption of this configuration, the components of the communication adjusting mechanism 6 are configured to be moved in the longitudinal direction of the body-insertable apparatus in order to generate the pressing force in the longitudinal direction of the body-insertable apparatus, which allows the communication adjusting mechanism 6 to be miniaturized with respect to the direction orthogonal to the longitudinal direction of the body-insertable apparatus. As a result, the outer diameter of the body-insertable apparatus can be decreased to miniaturize the body-insertable apparatus.

The first embodiment has the configuration in which at least the second communicating channel 5 is formed so as to be located at the central axis with respect to the longitudinal direction of the body-insertable apparatus. Therefore, the fluid stored in the reservoir 2 is released to the outside space in the longitudinal direction from extension of the central axis of the body-insertable apparatus. In the subject, generally the body-insertable apparatus is moved while the proceeding direction of the body-insertable apparatus coincides with the longitudinal direction of the body-insertable apparatus, so that the fluid stored in the reservoir 2 is released toward the direction parallel to the proceeding direction from the opening of the central axis extension of the body-insertable apparatus by forming the second communicating channel 5 so as to be located on the central axis of the body-insertable apparatus. Accordingly, it is possible to suppress the generation of the change in attitude of the body-insertable apparatus by the released fluid, and the first embodiment has the advantage that the body-insertable apparatus stably moved in the subject can be realized.

The portion formed by the reservoir, the first and second communicating channels, and the like, the communication adjusting mechanism, and the control portion are sequentially arranged in the first embodiment. Thus, the portion where the fluid exists, the mechanical portion, and the electrical control portion are arranged while separated from one another, so that the structure is simplified while assembly of the portions is improved. Therefore, the first embodiment has the advantage that the miniaturization can be achieved.

Modification

Then, a modification of the body-insertable apparatus according to the first embodiment will be described. As described above, the body-insertable apparatus according to the first embodiment is one which releases the fluid such as the medicine stored in the reservoir 2 into the outside space. In addition, the body-insertable apparatus which samples the fluid such as the body fluid existing in the outside space can be realized by the use of the structure shown in the first embodiment.

Figure 3:
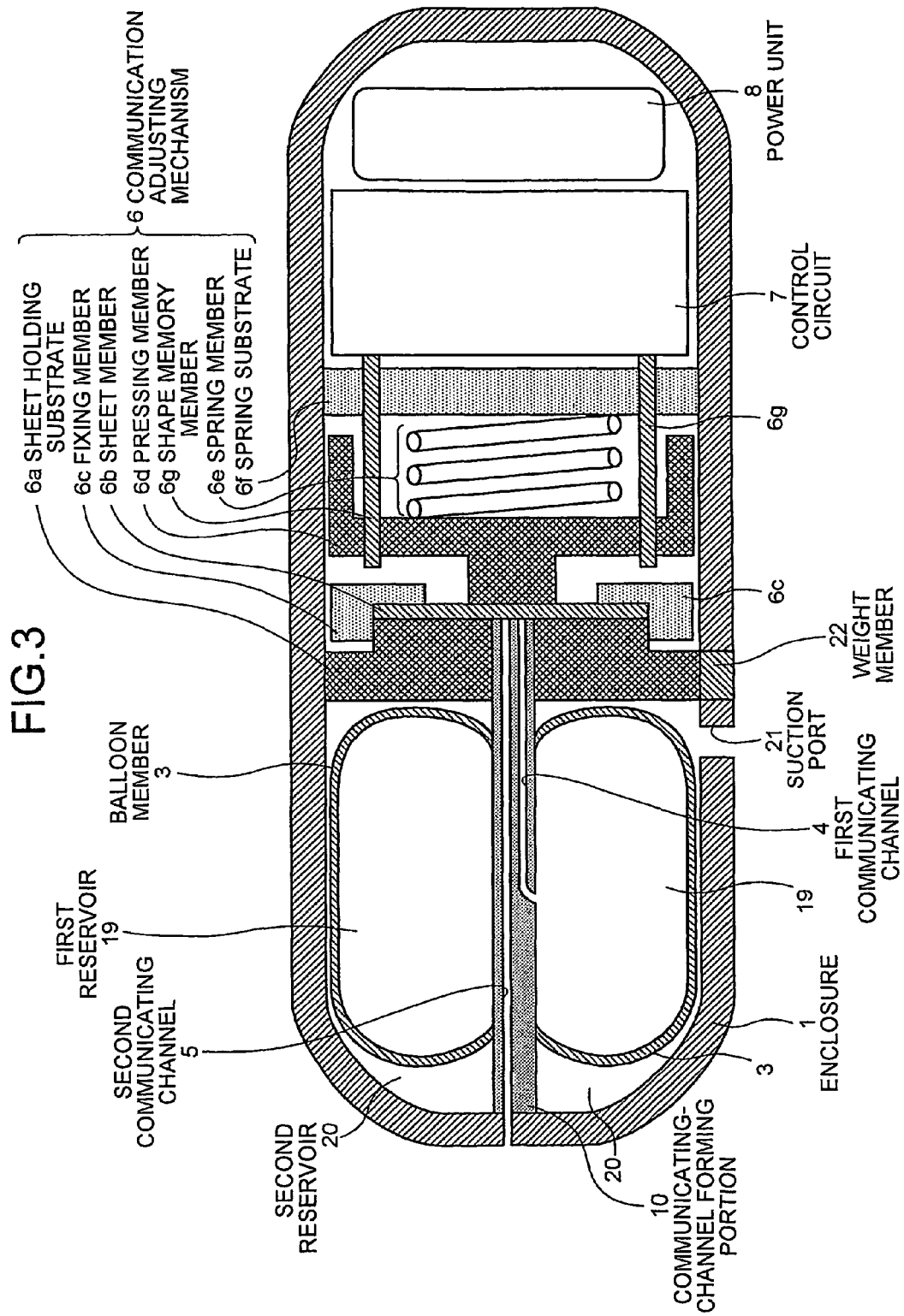
FIG. 3 is a sectional view schematically showing a configuration of a body-insertable apparatus according to a modification of the first embodiment.

FIG. 3 is a sectional view schematically showing a configuration of a body-insertable apparatus according to the modification. As shown in FIG. 3, the body-insertable apparatus according to the modification has the base basic structure as the first embodiment. However, in the structure of the body-insertable apparatus according to the modification, a first reservoir 19 is formed in the space region corresponding the reservoir 2 in the first embodiment while a second reservoir 20 is formed in the space region corresponding to the air space region 11, the vents 13 and 14 are neglected in the sheet holding substrate 6a, a suction port 21 communicating the second reservoir 20 and the outside space is formed in a part of the enclosure 1, and a weight member 22 is arranged near the suction port 21.

Similarly to the reservoir 2 in the first embodiment, the first reservoir 19 corresponds to the reservoir in claims, and the first reservoir 19 has the configuration in which the first reservoir 19 is substantially covered with the inner surface of the balloon member 3. The fluid which does not particularly act on the subject such as physiological saline rather than the medicine and the like is previously stored in the first reservoir 19. The second reservoir 20 is one in which the sampled fluid such as the body fluid is stored. In sampling the fluid, the fluid such as the body fluid in the outside space flows into the second reservoir 20 through the suction port 21.

The fluid sampling action performed by the body-insertable apparatus according to the modification will simply be described. As described in the first embodiment, the communication adjusting mechanism 6 is operated based on the current outputted from the control circuit 7, and the cavity portion is generated between the sheet holding substrate 6a and the sheet member 6b as a result of the operation of the communication adjusting mechanism 6. The first communicating channel 4 and the second communicating channel 5 are communicated through the cavity portion, the fluid previously stored in the first reservoir 19 is released to the outside space through the first communicating channel 4 and the second communicating channel 5, and the volume of the inner space of the first reservoir 19 is decreased according to the released amount of fluid.

At this point, in the second reservoir 20 which corresponds to the air space region 11 in the first embodiment, on the basis of the same reason as the air space region 11, the volume is increased according to the decrease in volume of the first reservoir 19. Since the negative pressure is generated inside the second reservoir 20 according to the increase in volume, the fluid such as the body fluid existing in the outside space of the body-insertable apparatus flows into the second reservoir 20 through the suction port 21. Thus, the body fluid existing in the outside space of the body-insertable apparatus is stored in the second reservoir 20, and the fluid sampling action is performed.

Then, the advantages of the body-insertable apparatus according to the modification will be described. The modification differs from the first embodiment which releases the medicine and the like, and the modification has the purpose of sampling the body fluid and the like existing in the outside space (that is, the inside of a digestive system and the like in the subject) of the body-insertable apparatus. However, the modification is similar to the first embodiment in the mechanism which moves the fluid, and the modification has the same basic structure as the first embodiment. Accordingly, as with the first embodiment, the body-insertable apparatus according to the modification has the advantage that the miniaturization can be achieved by extending the first communicating channel 4 and the second communicating channel 5 in the direction in which the first communicating channel 4 and the second communicating channel 5 are parallel to each other.

The body-insertable apparatus according to the modification has the structure in which the weight member 22 is arranged near the suction port 21. The weight member 22 is formed by the member whose specific gravity is larger than those of other members constituting the body-insertable apparatus, e.g., the enclosure 1. As a result, the body-insertable apparatus according to the modification maintains the state in which the suction port 21 is opened downward in a vertical direction in the subject. In the subject, because usually the body-insertable apparatus is moved while being in contact with the inner wall of the digestive system and the like located downward in the vertical direction, when the suction port 21 is opened downward in the vertical direction, the suction port 21 comes into contact with the inner wall of the digestive system and the like in sampling the body fluid and the like, which allows the body fluid and the like to be efficiently sampled.

The body-insertable apparatus can be sunk in the body fluid by setting the specific gravity of the body-insertable apparatus larger than that of the body fluid, which allows the body fluid to be securely sampled. The components inside the body-insertable apparatus may be arranged such that the center of gravity of the body-insertable apparatus is located near the suction port 21 while the weight member 22 is neglected.

Second Embodiment

Then, a body-insertable apparatus according to a second embodiment will be described. The body-insertable apparatus according to the second embodiment has the structure in which the volume of the reservoir is changed by an elastic force generated by the spring member, and the body-insertable apparatus has the function of releasing the fluid such as the medicine previously stored in the reservoir into the outside space in association with the volume change.

Figure 4:
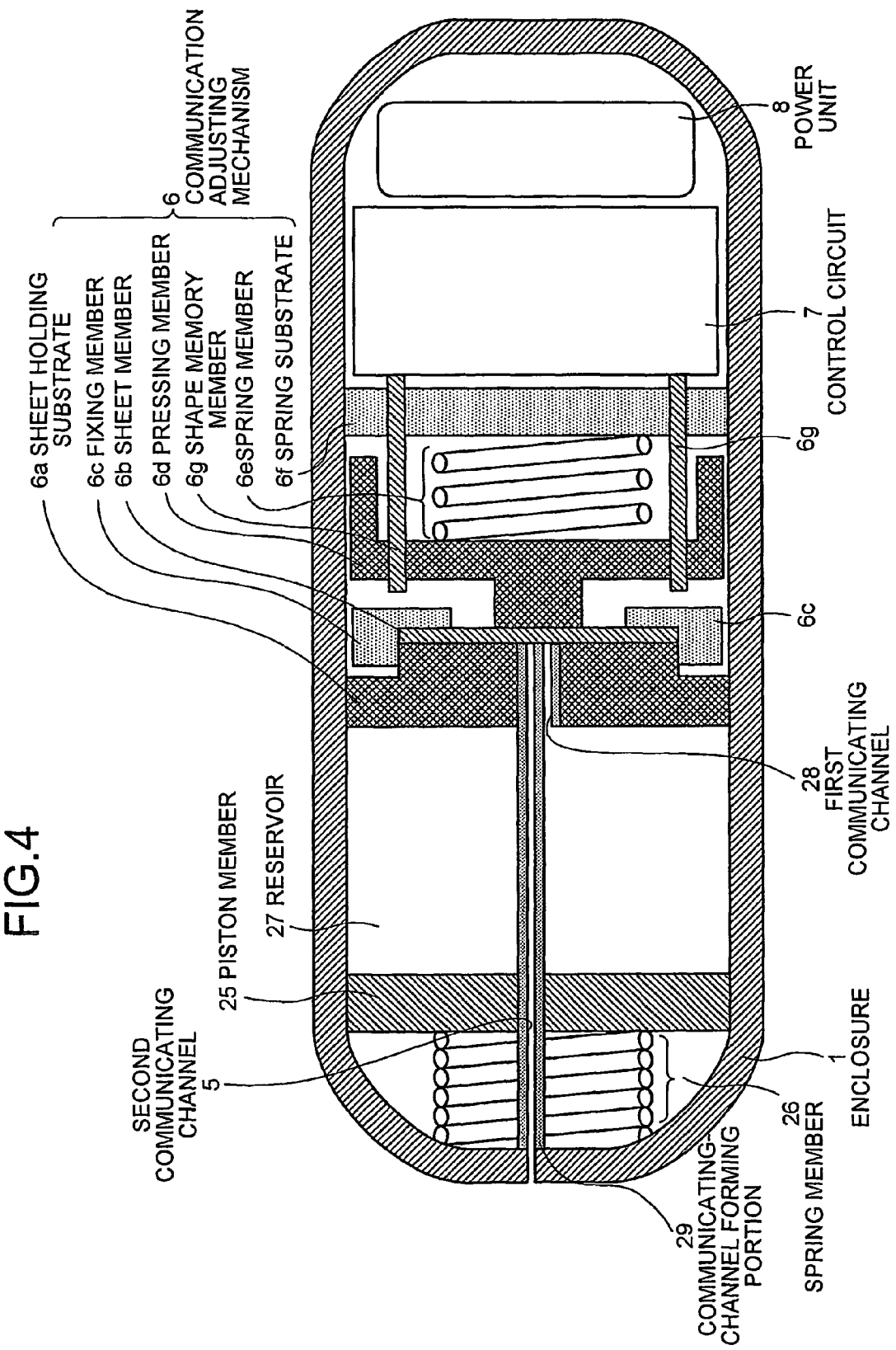
FIG. 4 is a sectional view schematically showing a configuration of a body-insertable apparatus according to a second embodiment.

FIG. 4 is a sectional view schematically showing a configuration of the body-insertable apparatus according to the second embodiment. As shown in FIG. 4, similarly to the first embodiment, the body-insertable apparatus according to the second embodiment includes the communication adjusting mechanism 6. However, the body-insertable apparatus according to the second embodiment differs from the first embodiment in the structures of the reservoir and the line communicating the reservoir and the outside space. Specifically, as shown in FIG. 4, the body-insertable apparatus according to the second embodiment includes a piston member 25 and a spring member 26. The piston member 25 is arranged in the opposite region (region located on the left side with respect to the sheet holding substrate 6a in FIG. 4) to the region, where the pressing member 6d and the like are arranged, to the sheet holding substrate 6a. The spring member 26 is arranged so as to bias the snapping force to the piston member 25 toward the direction in which the piston member 25 is brought close to the sheet holding substrate 6a. The body-insertable apparatus according to the second embodiment includes a reservoir 27 whose outer wall portions are formed by the sheet holding substrate 6a, the piston member 25, and the enclosure 1 located between the sheet holding substrate 6a and the piston member 25. The body-insertable apparatus according to the second embodiment has the structure in which the body fluid such as the medicine is previously stored in the space region surrounded by such the outer wall portions.

In the body-insertable apparatus according to the second embodiment, the second communicating channel 5 and a first communicating channel 28 are formed as the line which communicates the reservoir 27 and the outside space. Similarly to the first embodiment, the second communicating channel 5 is formed such that one end is opened toward the outside space while the other end is opened in the surface of the sheet holding substrate 6a. The first communicating channel 28 is formed such that one end is opened to the inside of the reservoir 27 while the other end is opened in the surface of the sheet holding substrate 6a.

The first communicating channel 28 has the same function as the first communicating channel 4 in the first embodiment. However, the first communicating channel 28 differs from the first communicating channel 4 in the first embodiment in the structure in which the extended length becomes the length piercing through the sheet holding substrate 6a. In the second embodiment, a part of the outer wall portion of the reservoir 27 is formed by the sheet holding substrate 6a and one end of the first communicating channel 28 can be opened to the inside space of the reservoir 27 by making the opening in the backside of the sheet holding substrate 6a, which results in the difference in structure. As can be seen from comparison of FIGS. 1 and 4, the structure of the first communicating channel 4 in FIG. 1 may be adopted instead of the first communicating channel 28.

Then, an action of the body-insertable apparatus according to the second embodiment will be described. The communication adjusting mechanism 6 functions so as to maintain the state in which the sheet member 6b is in close contact with the first communicating channel 28 and the second communicating channel 5 while the predetermined current is not outputted from the control circuit 7. On the other hand, when the body-insertable apparatus reaches the predetermined position in the subject, the control circuit 7 supplies the predetermined current, the position of the pressing member 6d is changed by changing the shape of the shape memory member 6g based on the current, and the sheet member 6b is released from the close contact state with the sheet holding substrate 6a.

As a result, the end portion of the first communicating channel 28 and the end portion of the second communicating channel 5 are communicated through the cavity portion generated between the surface of the sheet holding substrate 6a and the sheet member 6b, and the reservoir 27 and the outside space are communicated by communicating the first communicating channel 28 and the second communicating channel 5. As described above, since the spring member 26 supplies the snapping force to the piston member 25 which forms a part of the outer wall portion of the reservoir 27, the piston member 25 is moved toward the direction in which the piston member 25 is brought close to the sheet holding substrate 6a by communicating the inside of the reservoir 27 and the outside space of the body-insertable apparatus, and the fluid such as the medicine stored in the reservoir 27 is pushed out by the movement of the piston member 25, which releases the fluid into the outside space through the first communicating channel 28 and the second communicating channel 5. Thus, the fluid releasing action is performed in the second embodiment.

Then, the advantages of the body-insertable apparatus according to the second embodiment will be described. Similarly to the first embodiment, the body-insertable apparatus according to the second embodiment has the structure, in which the first communicating channel 28 and the second communicating channel 5 are extended in the directions parallel to each other and the first communicating channel 28 and the second communicating channel 5 are opened in the same surface of the sheet member 6b. Accordingly, similarly to the first embodiment, the advantage of the body-insertable apparatus according to the second embodiment has the advantage that the body-insertable apparatus can be miniaturized because of the above reason.

As with the modification of the first embodiment, the second embodiment can also be formed in the structure in which the fluid such as the body fluid is sampled. Specifically, for example, the spring member 26 may be arranged on the sheet holding substrate 6a side with respect to the piston member 25 to give the snapping force to the piston member 25 in the direction in which the piston member 25 is separated away from the sheet holding substrate 6a. In this structure, when the first communicating channel 28 and the second communicating channel 5 are communicated, the piston member 25 is moved in the direction in which the volume of the reservoir 27 is increased, which causes the negative pressure in the reservoir 27. Therefore, the fluid such as the body fluid existing in the outside space flows into the reservoir 27 through the second communicating channel 5 and the first communicating channel 28.

Third Embodiment

Then, a body-insertable apparatus according to a third embodiment will be described. The body-insertable apparatus according to the third embodiment includes a pump instead of the communication adjusting mechanism, and the body-insertable apparatus adopts the configuration in which the fluid such as the medicine previously stored in the reservoir is released into the outside space by the pump action.

Figure 5:
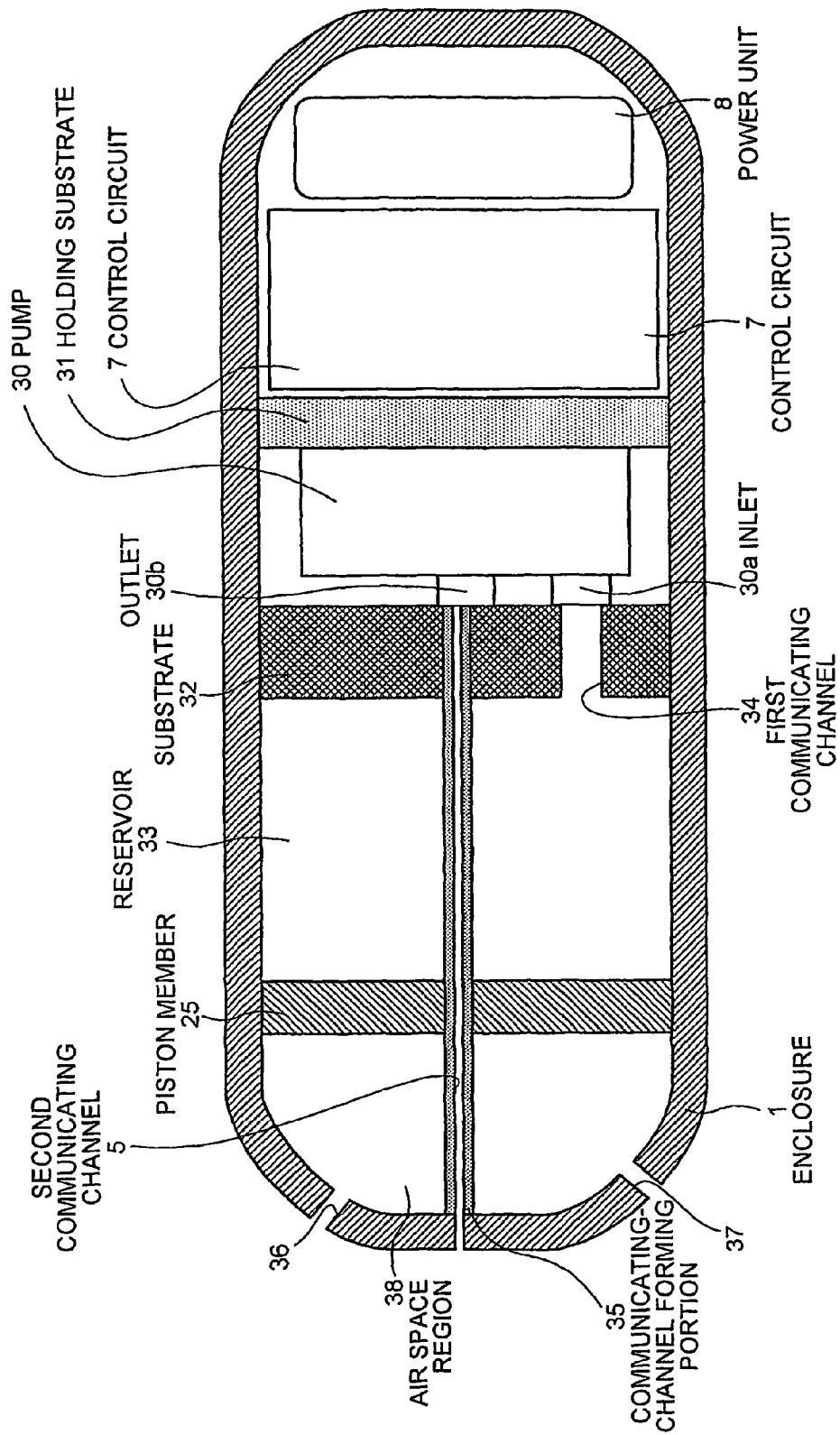
FIG. 5 is a sectional view schematically showing a configuration of a body-insertable apparatus according to a third embodiment.

FIG. 5 is a sectional view schematically showing a configuration of the body-insertable apparatus according to the third embodiment. As shown in FIG. 5, similarly to the first and second embodiments, the body-insertable apparatus according to the third embodiment includes the control circuit 7 and the power unit 8. However, the body-insertable apparatus according to the third embodiment is configured to have a pump 30 instead of the communication adjusting mechanism 6 in the first embodiment and the like, and the body-insertable apparatus according to the third embodiment differs from the first embodiment and the like in the structures of the reservoir and the like.

Specifically the pump 30 includes an inlet 30a which inputs the fluid and an outlet 30b which releases the fluid inputted through the inlet 30a again, and the pump 30 is arranged while fixed to a holding substrate 31 corresponding to the spring substrate 6f in the first embodiment and the like.

With reference to the reservoir and the like, the body-insertable apparatus according to the third embodiment also has the configurations different from the first embodiment and the like. Specifically, similarly to the sheet holding substrate 6a in the first embodiment and the like, the body-insertable apparatus according to the third embodiment includes a substrate 32 which is arranged while the end portion of the substrate 32 is in contact with the inner surface of the enclosure 1, a reservoir 33 is formed by the substrate 32, the piston member 25, and a part of the enclosure 1 located between the substrate 32 and the piston member 25, and the fluid such as the medicine is previously stored in the space region covered with the substrate 32 and the like. With reference to an air space region 38 which is formed on the side of the piston member 25 which is opposite the reservoir 33, the body-insertable apparatus according to the third embodiment has the structure in which vents 36 and 37 are formed in a part of the enclosure 10 in order to suppress the generation of the negative pressure in association with the movement of the piston member 25.

In a communicating channel forming member 35, the body-insertable apparatus according to the third embodiment has the second communicating channel 5, in which one end is opened to the outside space of the body-insertable apparatus while the other end is opened in the surface (surface on the side where the pump 30 is arranged) of the substrate 32. In the substrate 32, the body-insertable apparatus according to the third embodiment has a first communicating channel 34, in which one end is opened to the inside of the reservoir 33 while the other is opened in the surface of the substrate 32. In the third embodiment, the first communicating channel 34 and the second communicating channel 5 are formed such that the other end of the second communicating channel 5 is coupled to the outlet 30b of the pump 30 and the other end of the first communicating channel 34 is coupled to the inlet 30a of the pump 30. Similarly to the first embodiment and the like, the first communicating channel 34 and the second communicating channel 5 are formed so as to be extended in the directions parallel to each other.

The action of the body-insertable apparatus according to the third embodiment will briefly be described. Specifically the pump 30 is started to drive based on the control of the control circuit 7, and the pump is operated so as to output the fluid located on the inlet 30a side from the outlet 30b. As described above, in the third embodiment, since the first communicating channel 34 is formed corresponding to the inlet 30a, and the second communicating channel 5 is formed corresponding to the outlet 30b, when the pump 30 is started to drive, the fluid stored in the reservoir 33 communicated with the first communicating channel 34 is inputted to the pump 30 through the first communicating channel 34 and the inlet 30a, and the fluid is released into the outside space through the outlet 30b and the second communicating channel 5.

Thus, the same advantage as the first and second embodiments can be obtained even if the body-insertable apparatus is formed with the pump 30. That is, since the third embodiment also has the structure in which the first communicating channel 34 and the second communicating channel 5 are extended in the directions parallel to each other, the miniaturization of the body-insertable apparatus can be realized.

In the third embodiment, the first communicating channel 34 and the second communicating channel 5 are formed by the individual members in at least the example in the third embodiment. However, the advantage in the third embodiment is never lost by the structure shown in FIG. 5. That is, in the third embodiment, the reason why the first communicating channel 34 is formed in the substrate 32 is only that one of the end portions of the first communicating channel 34 is required to be coupled to the inlet 30a of the pump 30. In the pump 30, when the inlet 30a and the outlet 30b are configured to be arranged at the positions where the inlet 30a and the outlet 30b are brought close to each other, similarly to the first and second embodiments, the first communicating channel 34 can be formed on the same member as the second communicating channel 5. In the third embodiment, the outer diameter of the body-insertable apparatus is mainly determined by the structure of the pump 30, and it is not necessary that the first communicating channel 34 is formed at the position where the first communicating channel 34 is separated from the central axis in the longitudinal direction of the body-insertable apparatus farther than the outer periphery of the pump 30 because of the structure of the body-insertable apparatus. Therefore, even if the first communicating channel 34 is formed on the different member, the body-insertable apparatus is never enlarged.

Fourth Embodiment

Then, a body-insertable apparatus according to the fourth embodiment will be described. Similarly to the body-insertable apparatus according to the first embodiment, the body-insertable apparatus according to the fourth embodiment has the structure in which the balloon member defines a part of the outer shape of the body-insertable apparatus while the space region covered with the balloon member is set to the reservoir.

Figure 6:
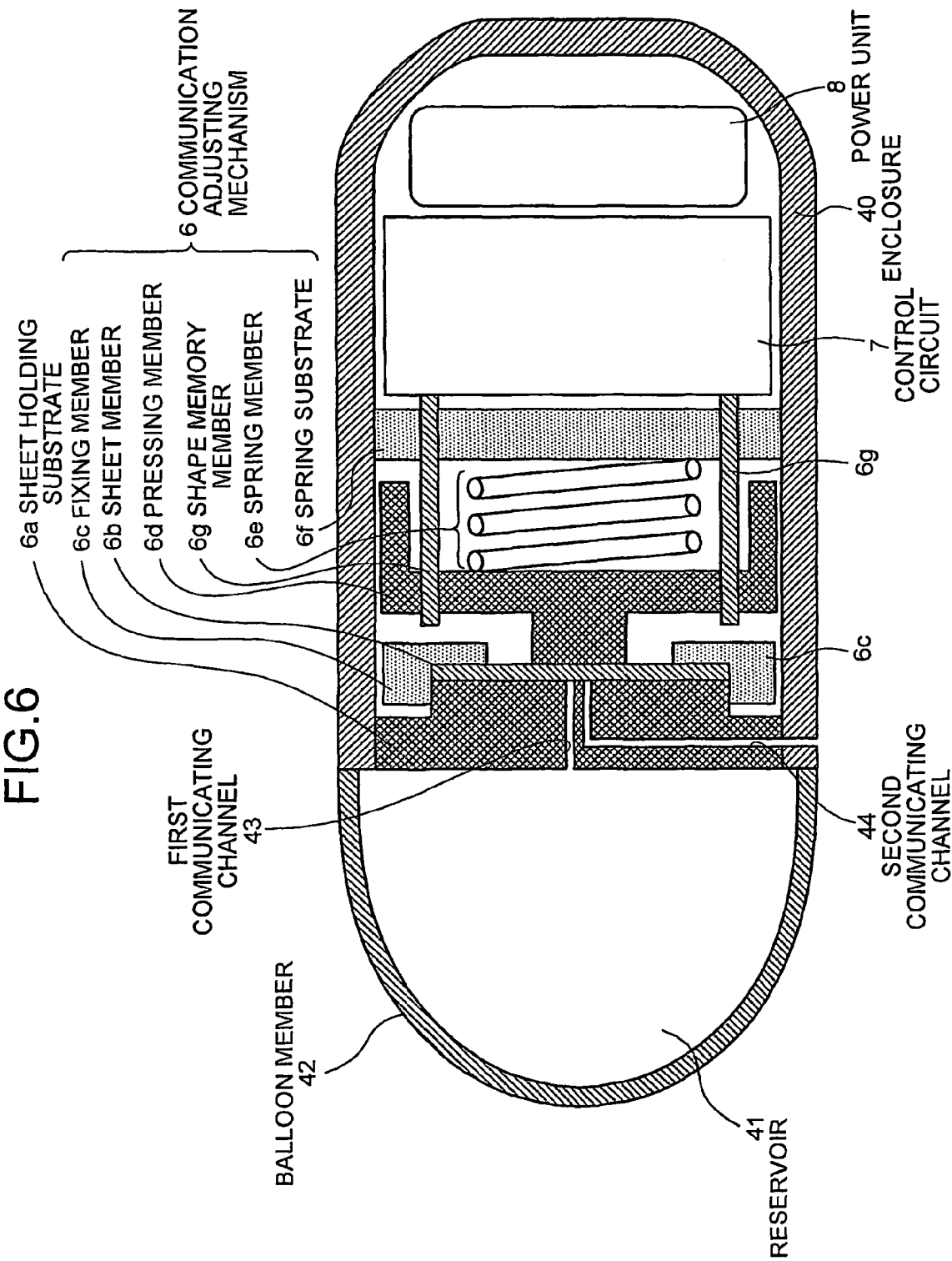
FIG. 6 is a sectional view schematically showing a configuration of a body-insertable apparatus according to a fourth embodiment.

FIG. 6 is a sectional view schematically showing a configuration of the body-insertable apparatus according to the fourth embodiment. As shown in FIG. 6, while the body-insertable apparatus according to the fourth embodiment includes the communication adjusting mechanism 6, the control circuit 7, and the power unit 8 which have the same structure as the first embodiment, the body-insertable apparatus according to the fourth embodiment includes an enclosure 40 and a balloon member 42. The enclosure 40 has the shape different from the first embodiment, and the balloon member 42 substantially forms the outer wall portion of a reservoir 41.

The enclosure 40 differs from the enclosure 1 in the first embodiment and the like in that the enclosure 40 is formed while opened on side in which the balloon member 42 is arranged. The sheet holding substrate 6a constituting the communication adjusting mechanism 6 is arranged in the opening, and a first communicating channel 43 and a second communicating channel 44 are formed in the sheet holding substrate 6a.

Similarly to the first communicating channel 4 in the first embodiment, the first communicating channel 43 is formed such that one end is opened to the inside of the reservoir 41 while the other end is opened in the surface (surface in which sheet member 6b is arranged) of the sheet holding substrate 6a. The second communicating channel 44 is formed such that one end is opened to the outside space while the other end is opened in the surface of the sheet holding substrate 6a.

Similarly to the balloon member 3 in the first embodiment, the balloon member 42 is made of the elastic material such as the rubber, and the balloon member 42 substantially forms the outer wall portion of the reservoir 41. However, the balloon member 42 differs from the first embodiment in that the outer shape of the body-insertable apparatus is defined. Specifically the balloon member 42 has the structure in which the end portion is fixed to the portion near the opening of the enclosure 40, and the balloon member 42 is formed such that the inside (namely, the reservoir 41) is not communicated with the space regions except for the first communicating channel 43. Thus, the reservoir 41 having the above structure is included, and the fluid releasing action is performed by the same action as the first embodiment. That is the first communicating channel 43 and the second communicating channel 44 are communicated based on the current outputted by the control circuit 7, the fluid stored in the reservoir 41 flows into the first communicating channel 43 by the contraction action of the balloon member 42, and the fluid is released into the outside space through the first communicating channel 43 and the second communicating channel 44.

In the body-insertable apparatus according to the fourth embodiment, similarly to the first communicating channel 4 and the second communicating channel 5 in the first embodiment, the first communicating channel 43 and the second communicating channel 44 are formed in the same member (sheet holding substrate 6a), and the first communicating channel 43 and the second communicating channel 44 are opened in the same surface (surface of the sheet holding substrate 6a), and the first communicating channel 43 and the second communicating channel 44 are extended in the direction parallel to each other near the end portion in which the opening is formed. Accordingly, in the fourth embodiment, the same advantage as the first embodiment and the like can be obtained based on the above similarities.

The fourth embodiment has the structure in which the balloon member 42 defines the outer shape of the body-insertable apparatus. As described above, the balloon member 42 forms the outer wall portion of the reservoir 41 and the balloon member 42 is contracted during the fluid releasing action, so that the occupied region of the balloon member 42 is decreased by performing the fluid releasing action, and finally the balloon member 42 comes into close contact with the backside of the sheet holding substrate 6a. As a result, the whole volume of the body-insertable apparatus is decreased when compared with the case in which the fluid is stored in the reservoir 41, and the body-insertable apparatus according to the fourth embodiment has the advantage that the miniaturization can further be achieved after releasing the fluid Fifth Embodiment Then, a body-insertable apparatus according to a fifth embodiment will be described. The fifth embodiment and subsequent embodiments has the feature in a mechanism which adjusts the communication state between the first communicating channel and the second communicating channel (namely, the mechanism corresponding to the communication adjusting mechanism 6 in the first embodiment), so that mainly the feature portions will be schematically shown in the drawings from FIG. 7 corresponding to the fifth embodiment and the subsequent embodiments. Although other components except for the mechanism which adjust the communication state such as the first communicating channel and the second communicating channel are described with reference to the first embodiment by way of example, as is clear from the following description, the structures shown in the drawings from FIG. 7 can obviously be applied to the structures of the body-insertable apparatus in the second embodiment and the like.

Figure 7:
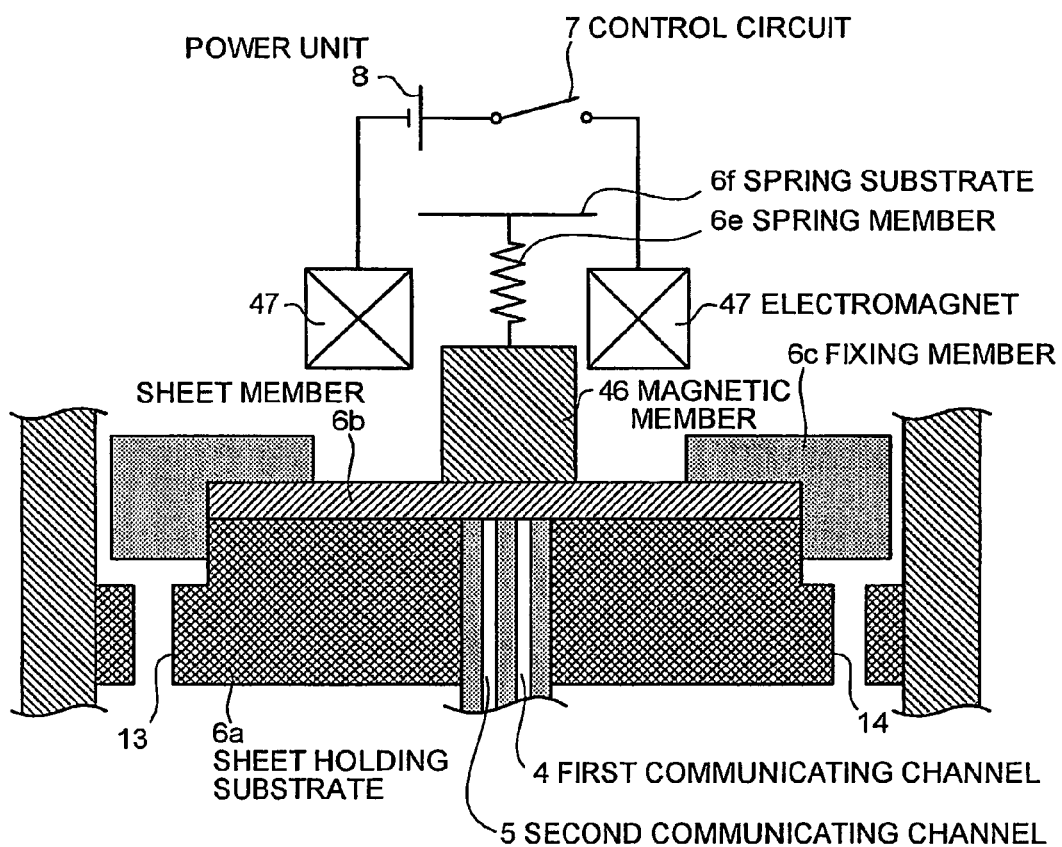
FIG. 7 is a schematic view showing a feature part of a body-insertable apparatus according to a fifth embodiment.

FIG. 7 is a schematic view showing a feature part of the body-insertable apparatus according to the fifth embodiment. As shown in FIG. 7, in the fifth embodiment, a magnetic member 46 is used as the pressing member. Further, the fifth embodiment has the configuration in which, instead of the shape memory member 6g, an electromagnet 47 is used as the member for changing the position of the magnetic member 46 in releasing and/or sampling the fluid.

The magnetic member 46 is formed by the member having predetermined magnetic properties, and the magnetic member 46 is made of the metal material such as iron. Similarly to the first embodiment and the like, before and after releasing and/or sampling the fluid, the magnetic member 46 applies the pressing force such that the elastic force from the spring member 6e causes the sheet member 6b to come into close contact with the sheet holding substrate 6a.

The electromagnet 47 is one which changes the position of the magnetic member 46 in releasing the fluid. Specifically, the electromagnet 47 has the structure in which a predetermined coil and the like are provided. Further, in the function of the electromagnet 47, the current is supplied from the power unit 8 based on the control of the control circuit 7, the magnetic force is generated based on the supplied current, and the magnetic member 46 is moved toward the direction in which the magnetic member 46 is separated away from the sheet member 6b.

The magnetic member 46 and the sheet member 6b may be integrated by bonding or the like. In this case, when the magnetic member 46 is attracted by the electromagnet 47, since the sheet member 6b in also moved along with the magnetic member 46, the communication can be realized more securely between the first communicating channel and the second communicating channel.

Sixth Embodiment

Then, a body-insertable apparatus according to a sixth embodiment will be described. The body-insertable apparatus according to the sixth embodiment has the structure in which the pressing force against the sheet member 6b is changed not by the position change, but by the shape change with respect to the member corresponding to the pressing member.

Figure 8:
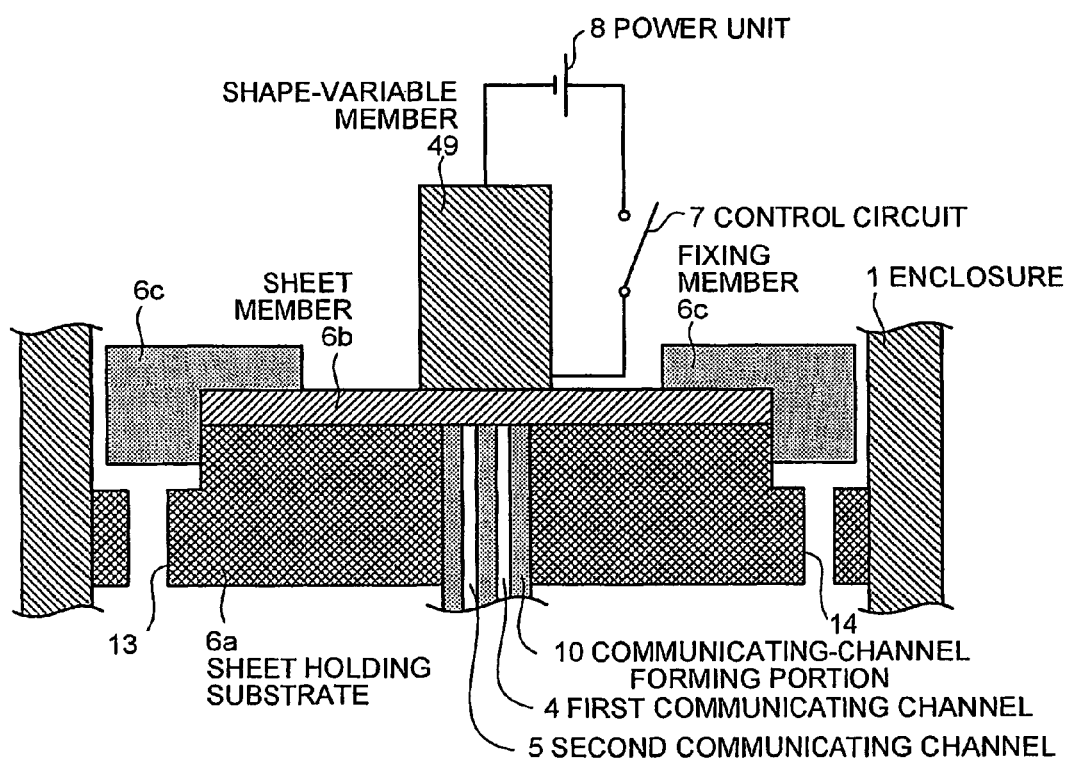
FIG. 8 is a schematic view showing a feature part of a body-insertable apparatus according to a sixth embodiment.

FIG. 8 is a schematic view showing a feature part of the body-insertable apparatus according to the sixth embodiment. As shown in FIG. 8, the sixth embodiment includes a shape-variable member 49 whose shape is changed based on the control of the control circuit 7, and the sixth embodiment has the structure in which the current supplied from the power unit 8 is directly supplied to the shape-variable member 49.

The shape-variable member 49 is made of the material, such as a piezoelectric element and an electrically conductive polymer, in which the shape is changed according to the supplied current. Specifically, in the shape-variable member 49, the surface opposing to the surface which comes into contact with the sheet member 6b is fixed to the enclosure 1. The shape-variable member 49 has the characteristics in which the length is decreased with respect to the longitudinal direction of the body-insertable apparatus such that the pressing force against the sheet member 6b is decreased or eliminated in supplying the current while the sufficient pressing force is applied to the sheet member 6b in not supplying the current. Since the shape-variable member 49 has the shape changing property as described above, in the body-insertable apparatus according to the sixth embodiment, the first communicating channel 4 and the second communicating channel 5 can be communicated during the current supply through the control circuit 7.

Figure 9:
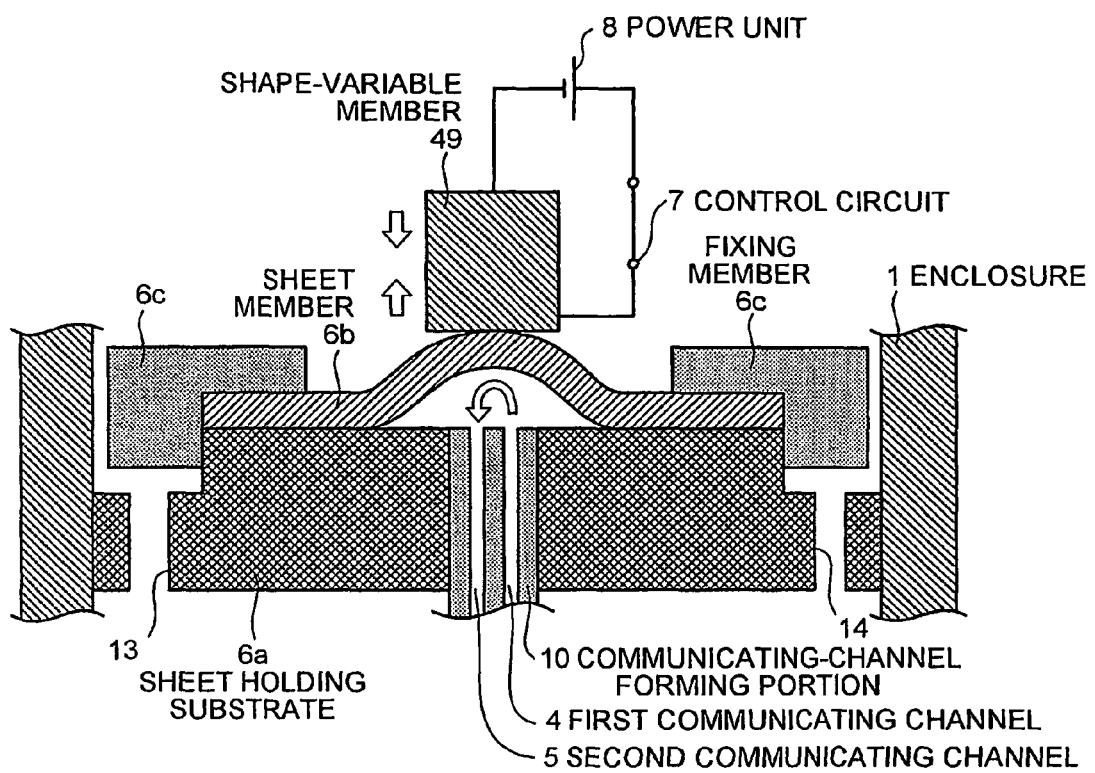
FIG. 9 is a schematic view for explaining an action of the body-insertable apparatus according to the sixth embodiment.

FIG. 9 is a schematic view for explaining an action of the body-insertable apparatus according to the sixth embodiment. As shown in FIG. 9, the current is supplied from the power unit 8 through the control circuit 7, which decreases the length of the shape-variable member 49 with respect to the longitudinal direction of the body-insertable apparatus. Therefore, the air space region is generated between the sheet member 6b and the sheet holding substrate 6a, which allows the communication between the first communicating channel 4 and the second communicating channel 5.

Seventh Embodiment

Then, a body-insertable apparatus according to a seventh embodiment will be described. Instead of the sheet member 6b in the first embodiment and the like, the body-insertable apparatus according to the seventh embodiment is configured to include a shape-variable sheet whose shape is changed based on the supplied current.

Figure 10:
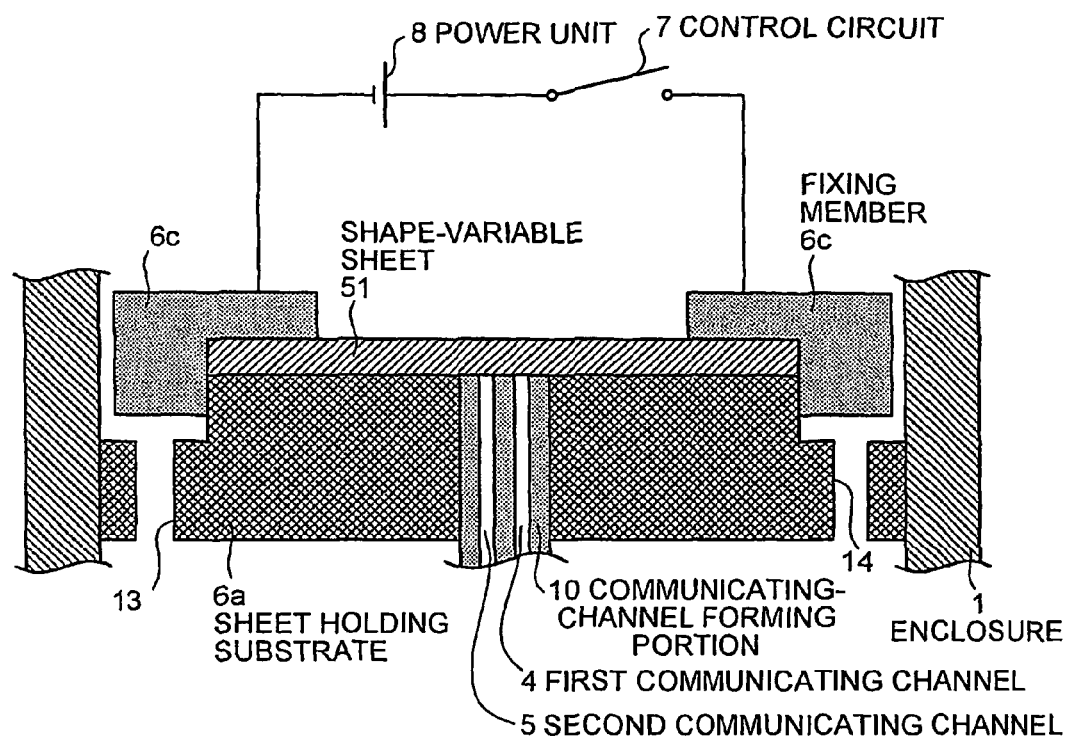
FIG. 10 is a schematic view showing a feature part of a body-insertable apparatus according to a seventh embodiment.

FIG. 10 is a schematic, view showing a feature part of the body-insertable apparatus according to the seventh embodiment. As shown in FIG. 10, the body-insertable apparatus according to the seventh embodiment includes a shape-variable sheet 51 instead of the sheet member 6b. Further, in the configuration of the body-insertable apparatus according to the seventh embodiment, while the current supplied through the control circuit 7 is directly supplied to the shape-variable sheet 51, the pressing member, the spring member, and the like are neglected.

The shape-variable sheet 51 is made of the material having the property in which the shape is changed according to the current supply. For example, the shape-variable sheet 51 is made of the material such as the electrically conductive polymer and the shape memory alloy. Specifically, in not supplying the current, similarly to the sheet member 6b, the shape-variable sheet 51 has the shape in which the shape-variable sheet 51 is in close contact with the sheet holding substrate 6a to block the end portions of the first communicating channel 4 and the second communicating channel 5 from other space regions. On the other hand, in supplying the current, the shape-variable sheet 51 is changed in the shape in which the shape-variable sheet 51 is separated from the sheet holding substrate 6a near the region where the end portions of the first communicating channel 4 and the second communicating channel 5 are formed. Alternatively, the member, in which the shape is changed in order to expand an area in supplying the current to form the resultant cavity near the end portions of the first communicating channel and the second communicating channel, may be used as the shape-variable sheet 51.

Figure 11:
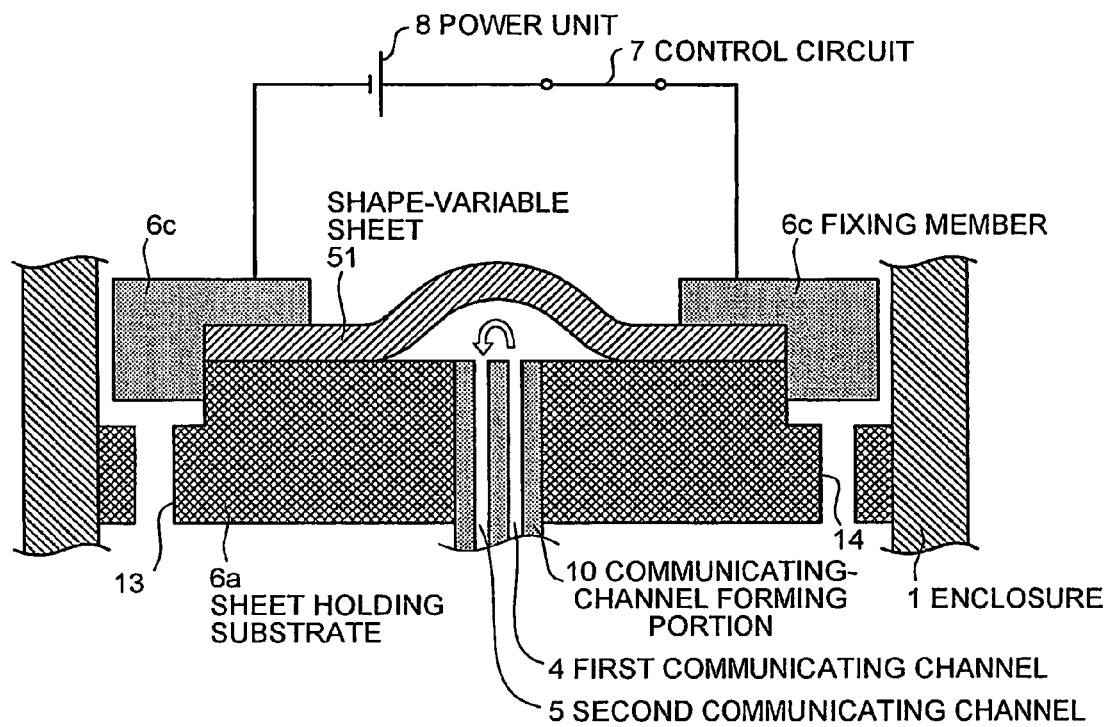
FIG. 11 is a schematic view for explaining an action of the body-insertable apparatus according to the seventh embodiment.

FIG. 11 is a schematic view for explaining an action of the body-insertable apparatus according to the seventh embodiment. As shown in FIG. 11, the current is supplied from the power unit 8 by the control of the control circuit 7, which allows the shape of the shape-variable sheet 51 to be changed near the first communicating channel 4 and the second communicating channel 5 such that the shape-variable sheet 51 is separated from the sheet holding substrate 6a. As a result, the first communicating channel 4 and the second communicating channel 5 are communicated to release the fluid stored in the reservoir 2 into the outside space through the first communicating channel 4 and the second communicating channel 5.

Thus, the body-insertable apparatus according to the seventh embodiment includes the shape-variable sheet 51 whose shape is changed according to the current supply, so that the pressing member 6d, the spring member 6e, the shape memory member 6g, and the spring substrate 6f can be neglected in the body-insertable apparatus according to the seventh embodiment. As can be seen from FIG. 1 and the like, the body-insertable apparatus can further be miniaturized by neglecting these components.

Eighth Embodiment

Then, a body-insertable apparatus according to an eighth embodiment will be described. Similarly to the body-insertable apparatus according to the first embodiment, the body-insertable apparatus according to the eighth embodiment includes the pressing member 6d and the like. However, the body-insertable apparatus according to the eighth embodiment includes a coupling member instead of the sheet member 6b.

Figure 12:
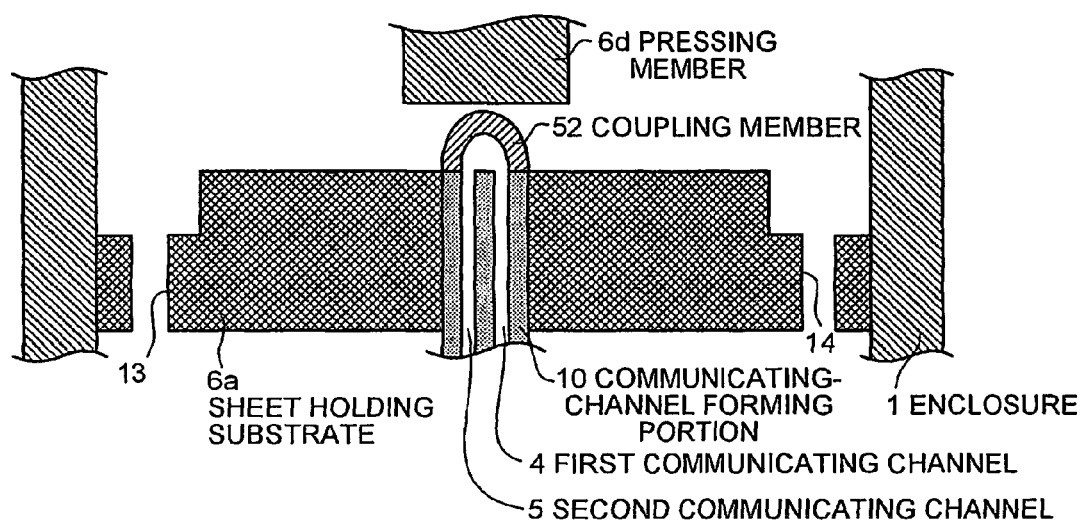
FIG. 12 is a schematic view showing a feature part of a body-insertable apparatus according to an eighth embodiment.

FIG. 12 is a schematic view showing a feature part of the body-insertable apparatus according to the eighth embodiment. As shown in FIG. 12, the body-insertable apparatus according to the eighth embodiment has the configuration including a coupling member 52 instead of the sheet member 6b.

Similarly to the sheet member 6b, the coupling member 52 is made of the watertight and flexible material, and the coupling member 52 is fixed to the end portion of the communicating channel forming portion 10. When the pressing force is not applied by the pressing member 6d, while the coupling member 52 communicates the first communicating channel 4 and the second communicating channel 5, the coupling member 52 includes the cavity portion whose communication state with other space regions is blocked. On the other hand, when the pressing force is applied by the pressing member 6d, the shape of the coupling member 52 is changed such that the cavity portion crushes. Similarly to the case in which the sheet member 6b is included, the communication state between the first communicating channel 4 and the second communicating channel 5 can be adjusted by including the coupling member 52.

Although the structure in which the communicating channel forming portion 10 and the coupling member 52 are separately formed by the individual members is adopted in the example shown in FIG. 12, the communicating channel forming portion 10 and the coupling member 52 may integrally be formed. That is, the communicating channel forming portion 10 and the coupling member 52, in which the flexible member is used, may integrally be formed. Therefore, the fixing member 6c and the like can be neglected by adopting the structure, and the body-insertable apparatus can further be miniaturized.

As described above, the invention is described over the first to eighth embodiments. However, the invention should not be interpreted while limited to the above embodiments, and those skilled in the art could make various embodiments and modifications. For example, with reference to the relationship between the communication adjusting mechanism and the communicating channel forming portion, the structure different from FIG. 1 and the like can also be adopted.

Figure 13:
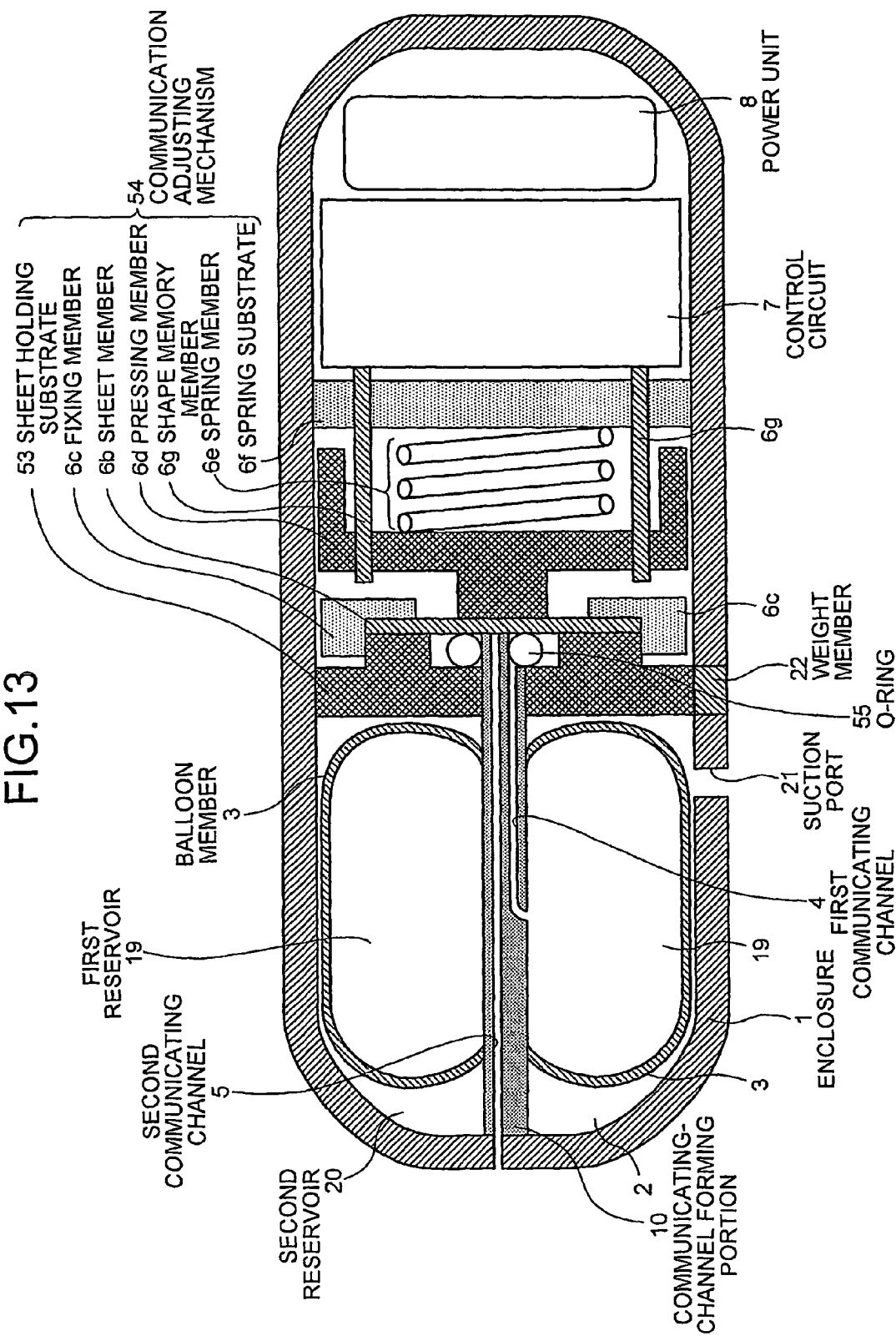
FIG. 13 is a sectional view schematically showing a configuration of a body-insertable apparatus according to a modification.

FIG. 13 is a sectional view schematically showing a body-insertable apparatus configuration in which a communication adjusting mechanism different from FIG. 1 and the like is adopted. As shown in FIG. 13, in the body-insertable apparatus shown in FIG. 13, a communication adjusting mechanism 54 which includes a sheet holding substrate 53 having a predetermined recess region is used instead of the communication adjusting mechanism 6. The sheet holding substrate 53 has the structure in which the recess region is formed in the region corresponding to the communicating channel forming portion 10. Specifically the recess region is formed near the central axis in the longitudinal direction of the body-insertable apparatus, and the communicating channel forming portion 10 is formed in the central axis in the longitudinal direction of the body-insertable apparatus. The first communicating channel 4 and the second communicating channel 5, formed in the communicating channel forming portion 10, are formed such that the end portions of the first communicating channel 4 and the second communicating channel 5 are opened in the recess region. In the recess region of the sheet holding substrate 53, an O-ring 55 (watertight member) is arranged near the region where the first communicating channel 4 and the second communicating channel 5 are formed. Even if this structure is adopted, the advantages described in the first to eighth embodiments can be obtained. In the body-insertable apparatus shown in FIG. 13, the structure of the body-insertable apparatus according to the modification of the first embodiment shown in FIG. 3 is employed. In addition to the modification of the first embodiment, for example, the communication adjusting mechanism 54 can obviously be used for the body-insertable apparatus according to the first embodiment instead of the communication adjusting mechanism 6.

Ninth Embodiment

Figure 14:
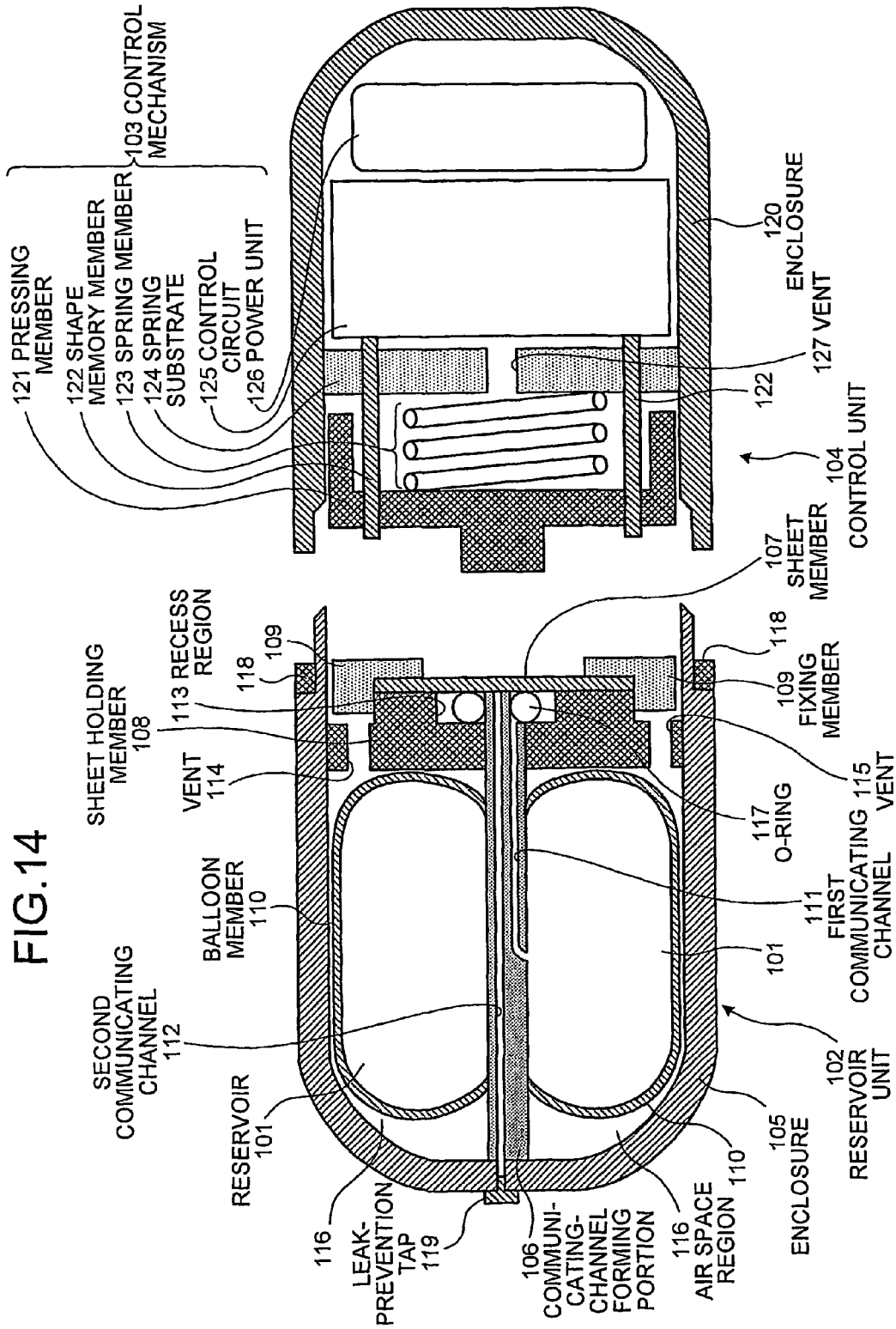
FIG. 14 is a schematic view showing a body-insertable apparatus according to a ninth embodiment while the body-insertable apparatus is divided into units.

First a body-insertable apparatus according to a ninth embodiment will be described. FIG. 14 is a schematic view showing the body-insertable apparatus according to the ninth embodiment while the body-insertable apparatus is divided into units. As shown in FIG. 14, the body-insertable apparatus according to the ninth embodiment includes a reservoir unit 102, a control mechanism 103, and a control unit 104. The reservoir unit 102 includes a reservoir 101 in which the fluid used for at least one of the input and the output to and from the subject is stored. The control mechanism 103 controls the input and the output of the fluid stored in the reservoir 101. The control unit 104 is formed so as to be detachable from the reservoir unit 102.

The reservoir unit 102 includes an enclosure 105 and components incorporated in the enclosure 105. In the enclosure 105, a portion to which the control unit 104 is mounted is opened. With reference to the components incorporated in the enclosure 105, the reservoir unit 102 includes the reservoir 101, a communicating channel forming portion 106, a sheet member 107, a sheet holding substrate 108, and a fixing member 109. The fluid used for at least one of the input and the output is stored in the reservoir 101. The communicating channel for communicating the reservoir 101 and the outside space of the body-insertable apparatus (hereinafter simply referred to as "outside space") is formed in the communicating channel forming portion 106. The sheet member 107 adjusts the communication state between the reservoir 101 and the outside space through the communicating channel based on the control of the control mechanism 103. The sheet holding substrate 108 holds the sheet member 107. The fixing member 109 fixes the sheet member 107 to the sheet holding substrate 108.

In the example of the ninth embodiment, the reservoir 101 is one which previously holds the fluid such as the medicine released into the subject. Specifically, the outer wall portion (portion defining the outer periphery of the storage region) of the reservoir 101 is formed by a balloon member 110 made of the elastic material such as the rubber, and the reservoir 101 has the function of storing the fluid in the inner space of the balloon member 110. In the ninth embodiment, the releasing action in which the stored fluid is pushed out to the outside space is performed by the contraction action of the balloon member 110 constituting the reservoir 101.

The communicating channel forming portion 106 is formed by the rod-shaped member arranged along the central axis in the longitudinal direction of the body-insertable apparatus according to the ninth embodiment, and communicating channel forming portion 106 has the configuration in which a first communicating channel 111 and a second communicating channel 112 are formed along the direction in which the rod-shaped member is extended. Specifically the first communicating channel 111 is formed such that one end is opened to the inside space of the reservoir 101 while the other end is opened to a recess region 113 (described later) formed in the sheet holding substrate 108. The second communicating channel 112 is formed such that one end is opened to the recess region formed in the sheet holding substrate 108 while the other end is opened to the outside space.

The sheet holding substrate 108 is one which holds the sheet member 107. Specifically, the sheet holding substrate 108 is arranged such that the inside space of the enclosure 105 is covered with the sheet holding substrate 108 near the opening (namely, portion coupled to the control unit 104) of the enclosure 105, and the sheet holding substrate 108 has the structure in which the recess region 113 is formed near the central axis in the longitudinal direction of the body-insertable apparatus according to the ninth embodiment. As described above, the recess region 113 is one in which the end portions of the first communicating channel 111 and the second communicating channel 112 are opened. In the recess region 113, the fluid stored in the reservoir 101 is released into the outside space by communicating the end portions of the first communicating channel 111 and the second communicating channel 112 based on the control of the control mechanism 103. In addition to the recess region 113, vents 114 and 115 are formed in the sheet holding substrate 108 so as to pierce in the longitudinal direction of the body-insertable apparatus according to the ninth embodiment. The vents 114 and 115 are one which communicates an air space region 116 with other regions. The air space region 116 is defined by the outer surface of the balloon member 110, the inner surface of the enclosure 105, and the backside (surface opposing to the surface in which the sheet member 107 is arranged) of the sheet holding substrate 108. The advantage generated by the provision of the vents 114 and 115 will be described in detail later.

The sheet member 107 is one which controls the communication state between the end portion, opened to the recess region 113, of the first communicating channel 111 and the end portion of the second communicating channel 112 based on the control of the control mechanism 103. Specifically, the sheet member 107 is arranged such that the recess region 113 is covered with the sheet member 107, and the sheet member 107 is made of the flexible and watertight membrane member. When the control mechanism 103 controls such that the releasing action of the fluid stored in the reservoir 101 is not performed, the sheet member 107 is kept in the state in which the sheet member 107 is in close contact with the end portion of the second communicating channel 112. On the other hand, when the fluid releasing action is performed, the sheet member 107 is formed so as to be separated from the end portion of the second communicating channel 112 by the control of the control mechanism 103. The communication state between the second communicating channel 112 and the first communicating channel 111 is controlled by separating and bringing the sheet member 107 from and close to the end portion of the second communicating channel 112 according to the control of the control mechanism 103, which allows the fluid releasing action to the outside space to be controlled. In order to aid the function (namely, the function of keeping the close contact state with the end portion of the second communicating channel 112) of the sheet member 107 when the fluid releasing action is not performed, an O-ring 117 is arranged near the end portion, opened to the recess region 113, of the second communicating channel 112.

As shown in FIG. 14, the pressing force is not applied to the sheet member 107 in the state in which the reservoir unit 102 and the control unit 104 are separated from each other, so that the sheet member 107 is separated from the end portion of the second communicating channel 112. Therefore, in the state in which the reservoir unit 102 and the control unit 104 are separated from each other, it is necessary to separately include a mechanism which prevents the leakage of the fluid stored the reservoir 101 to the outside space. Based on this perspective, the ninth embodiment adopts the configuration in which a leak-prevention tap 119 is inserted in the opening of the second communicating channel 112 to the outside space. The leak-prevention tap 119 prevents the communication between the second communicating channel 112 and the outside space, and the leak-prevention tap 119 prevents the leakage of the fluid.

The fixing member 109 is one which fixes the sheet member 107 to the sheet holding substrate 108. Specifically the fixing member 109 has the function of fixing the outer peripheral portion of the sheet member 107 to the sheet holding substrate 108 in a watertight contact manner. The arrangement of the fixing member 109 having the function described above prevents the communication of the recess region 113 covered with the sheet member 107 with other space regions except for the second communicating channel 112. The arrangement of the fixing member 109 also prevents the leakage of the fluid to other space regions except for the second communicating channel 112 through the first communicating channel 111 when the fluid is released.

Then, the control unit 104 will be described. The control unit 104 is one which controls the releasing action of the fluid stored in the reservoir 101 included in the reservoir unit 102. Specifically the control unit 104 includes the control mechanism 103 and an enclosure 120. The enclosure 120 holds the control mechanism 103 therein. In the enclosure 120, a portion to which the reservoir unit 102 is attached is opened.

The control mechanism 103 is one which controls the releasing action of the fluid stored in the reservoir 101. In the ninth embodiment, the control mechanism 103 controls the contact state of the sheet member 107 with the end portion, opened to the recess region 113, of the second communicating channel 112. Specifically the control mechanism 103 includes a pressing member 121, a shape memory member (shape-variable member) 122, a spring member 123, and a spring substrate 124. The pressing member 121 applied the pressing force to the sheet member 107 toward the direction in which the sheet member 107 is brought close to the second communicating channel 112. The shape memory member 122 adjusts the position of the pressing member 121 with respect to the sheet member 107. The spring member 123 generates the pressing force which is applied to the sheet member 107 by the pressing member 121. The spring substrate 124 holds the shape memory member 122 and the spring member 123. The control mechanism 103 includes a control circuit 125 and a power unit 26. The control circuit 125 controls the pressing force which is applied to the sheet member 107 by the pressing member 121. The power unit 126 supplies drive power of the control circuit 125.

The pressing member 121 has the function of adjusting the close contact state between the sheet member 107 and the end portion of the second communicating channel 112 by applying the pressing force to the sheet member 107. Specifically the pressing member 121 has the structure in which a projection region is formed near the central axis in the longitudinal direction of the body-insertable apparatus in the state in which the control unit 104 is attached to the reservoir unit 102, i.e., at the position corresponding to the recess region 113 formed in the sheet holding substrate 108. The pressing member 121 has the function of causing the projection region to abut on the sheet member 107 to apply the pressing force to the sheet member 107.

The shape memory member 122 is one which changes the position of the pressing member 121 with respect to the sheet member 107. Specifically the shape memory member 122 has the rod-shaped structure in which one end is fixed to the spring substrate 124 while the other end is fixed to the pressing member 121, and the shape memory member 122 is made of the shape memory alloy which has the predetermined electric resistance value while having the predetermined shape memory properties. More specifically the shape memory member 122 has the enough length to cause the pressing member 121 to abut onto the sheet member 107, e.g., under the temperature condition equal to the temperature inside the subject. On the other hand, the shape memory member 122 has the function in which the shape thereof is changed to separate the pressing member 121 from the sheet member 107 under the temperature condition that is sufficiently higher than the predetermined temperature, e.g., the temperature inside the subject.

The spring member 123 is one which generates the pressing force applied to the sheet member 107 by the pressing member 121. Specifically, in the spring member 123, one end is fixed to the spring substrate 124 while the other end is fixed to the pressing member 121, and a spring length is kept shorter than the natural length. Therefore, the spring member 123 has the function of biasing the snapping force to the pressing member 121 toward the direction in which the sheet member 107 is located (leftward direction in FIG. 9).

The spring substrate 124 is one which holds the spring member 123 and the shape memory member 122. A predetermined vent 127 is formed in the spring substrate 124, and the vent 127 keeps the communication state between the space regions to which both the surfaces of the spring substrate 124 are faced. As shown in FIG. 14, with respect to the spring substrate 124, the spring member 123 and the like are arranged on the reservoir unit 102 side (leftward in FIG. 14), and the control circuit 125 and the like are arranged on the opposite side (rightward in FIG. 14). The vent 127 has the function of communicating the space region where the spring member 123 and the like are arranged and the space region where the control circuit 125 is arranged.

The control circuit 125 has the function of outputting an electric signal defining the timing which starts the releasing action of the fluid stored in the reservoir 101. In the ninth embodiment, the control circuit 125 has the configuration in which the start timing is defined by outputting the predetermined current in the form of the electric signal to the shape memory member 122. That is, since the shape memory member 122 has the property in which the shape is changed according to the temperature, in the ninth embodiment, the control circuit 125 supplies the current to the shape memory member 122 at predetermined timing to generate the Joule heat, which changes the temperature of the shape memory member 122. As a result, the fluid releasing action is performed. For example, the configuration in which a timer mechanism is incorporated to start the current supply when a predetermined time elapses or the configuration in which mechanisms such as an antenna and a receiving circuit for receiving a wireless signal are incorporated to send the wireless signal including the control signal from the outside can be adopted as the configuration in which the current supply timing of the control circuit 125 is defined. The configuration in which a magnetic switch such as a reed switch is provided in the circuit and the power of the circuit is turned on to supply the current to the shape memory member 22 based on a magnetic field applied from the outside may be adopted.

The power unit 126 is one which supplies the drive power to the control circuit 125. Specifically, the power unit 126 is formed by a primary battery, and a rechargeable secondary battery may be used as the power unit 126 because the control unit 104 can be reused in the ninth embodiment as described later.

Then, a relationship between the enclosure 105 constituting the reservoir unit 102 and the enclosure 120 constituting the control unit 104 will be described. In the enclosure 105 and the enclosure 120, the outer diameters about the central axis in the longitudinal direction are substantially equal to each other. For example, the enclosure 105 and the enclosure 120 have the structures in which one of the enclosure 105 and the enclosure 120 is attachable to the other in a mechanical manner such as a screw-thread method or a machine-screw method. Specifically, for example, while an external thread is formed on the outer peripheral surface near the opening in the enclosure 105, an internal thread corresponding to the external thread is formed on the inner peripheral surface near the opening in the enclosure 120, and the external thread and the internal thread are coupled to each other when the enclosure 105 is attached to the enclosure 120. Therefore, the control unit 104 is detachable from the reservoir unit 102.

Specifically assembly of the body-insertable apparatus according to the ninth embodiment is performed as follows. The control unit 104 is attached to the reservoir unit 102 which is in the state shown in FIG. 14 by the screw coupling or the like. Then, the leak-prevention tap 119 is taken out from the opening formed in the reservoir unit 102 to the outside space of the second communicating channel 112, which allows the second communicating channel 112 and the outside space to be changed to the communicated state to finish the assembly of the body-insertable apparatus.

Figure 15:
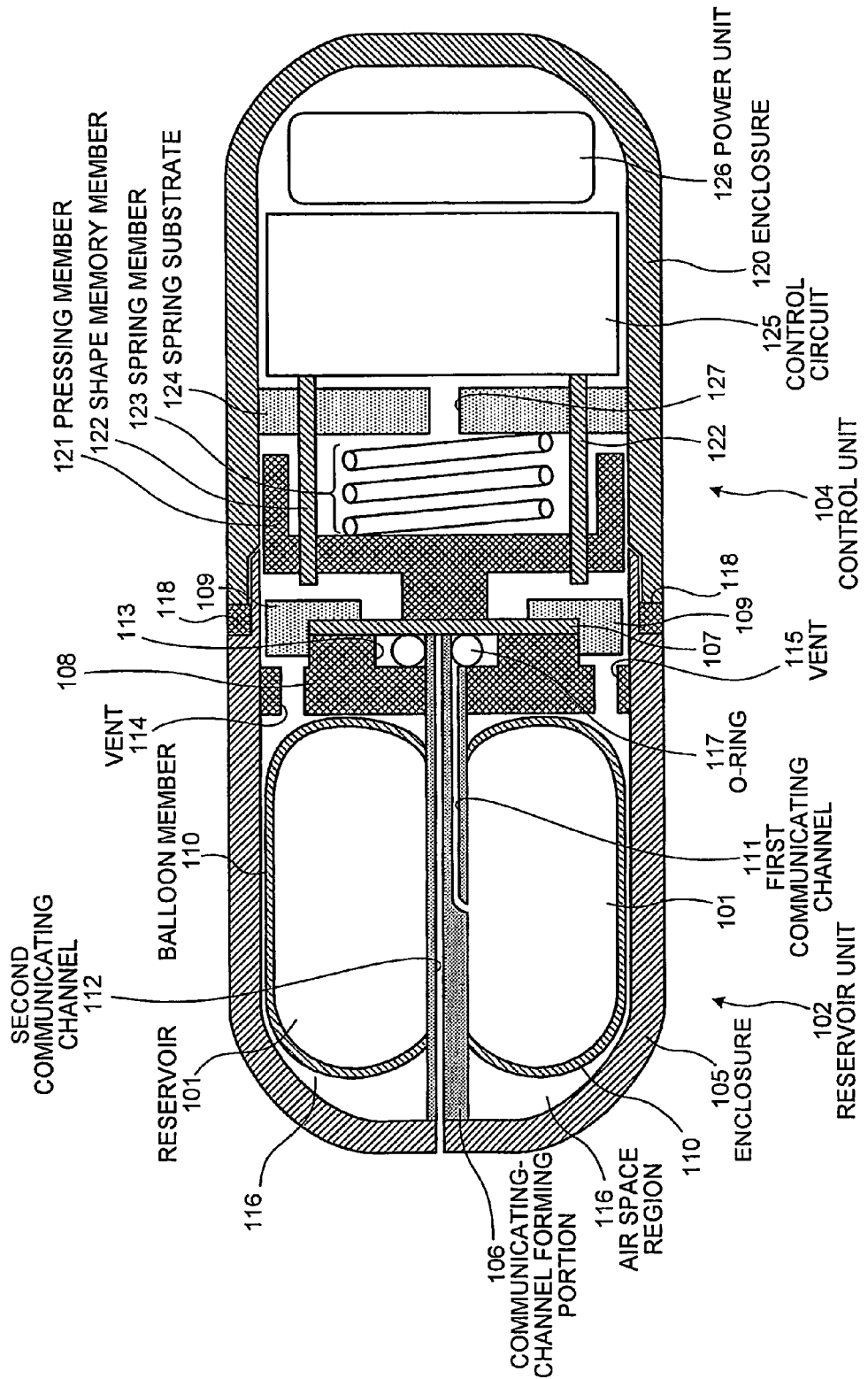
FIG. 15 is a schematic view showing a configuration of the body-insertable apparatus while the units are connected.

FIG. 15 is a schematic view showing the state in which the control unit 104 is attached to the reservoir unit 102. As shown in FIG. 15, the enclosure 105 constituting the reservoir unit 102 and the enclosure 120 constituting the control unit 104 are mechanically coupled to each other, which allows the reservoir unit 102 and the control unit 104 to be integrated in the body-insertable apparatus according to the ninth embodiment. Because a watertight rubber member 118 is arranged between the enclosure 105 and the enclosure 120, the fluid can be prevented from invading the inside through the coupling portion between the enclosure 105 and the enclosure 120. As shown in FIG. 15, when the control unit 104 is attached to the reservoir unit 102, the pressing member 121 abuts onto the sheet member 107, and the predetermined pressing force is applied by the pressing member 121. Therefore, as described above, the sheet member 107 is kept in the state in which the sheet member 107 is in close contact with one end of the second communicating channel 112 unless the control mechanism 103 controls such that the releasing action is performed, which allows the leak-prevention tap 119 to be taken off from the other end of the second communicating channel 112.

Then, an action of the body-insertable apparatus according to the ninth embodiment will be described. Before the body-insertable apparatus according to the ninth embodiment is introduced into the subject and after the body-insertable apparatus is discharged from the subject, as shown in FIG. 14, the body-insertable apparatus is kept while the reservoir unit 102 and the control unit 104 are separated from each other. On the other hand, as shown in FIG. 15, the body-insertable apparatus is used while the control unit 104 is attached to the reservoir unit 102, when the body-insertable apparatus is introduced and used in the subject.

Figure 16:
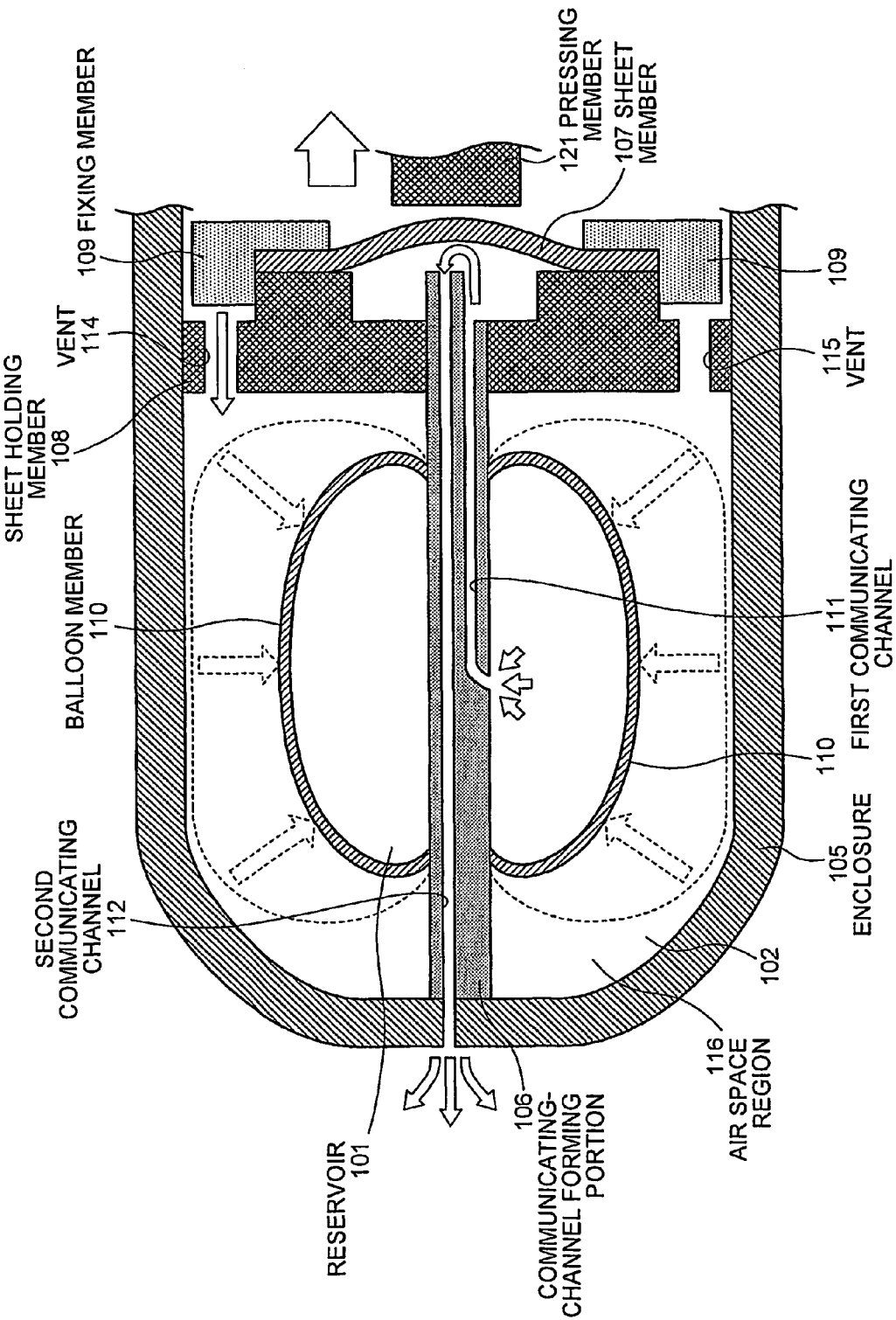
FIG. 16 is a schematic view for explaining an action of the body-insertable apparatus.

FIG. 16 is a schematic view for explaining the fluid releasing action performed by the body-insertable apparatus according to the ninth embodiment. The action of the body-insertable apparatus will be described below with reference to FIG. 16.

The control circuit 125 included in the control mechanism 103 supplies the current to the shape memory member 122, the shape memory member 122 generates the Joule heat therein based on the supplied current because the shape memory member 122 is the conductive member having the predetermined electrical resistance, the temperature of the shape memory member 122 is raised, and the shape of the shape memory member 122 is changed according to the shape memory property. Specifically, the shape memory member 122 is previously formed such that the length in the longitudinal direction contracts according to the temperature rise. As shown in FIG. 16, the pressing member 121 fixed to one end of the shape memory member 122 is moved toward the direction (rightward direction in FIG. 16) in which the pressing member 121 is separated from the sheet member 107 according to the contraction of the length in the longitudinal direction of the shape memory member 122, and the pressing force applied to the sheet member 107 is decreased or eliminated.

When the pressing force applied to the sheet member 107 is decreased or eliminated, the close contact state between the sheet member 107 and the end portion of the second communicating channel 112 is released as shown in FIG. 16, which allows the end portion of the second communicating channel 112 and the end portion of the first communicating channel 111 to be communicated in the recess region 113. As described above, the other end of the second communicating channel 112 is opened to the outside space, and the other end of the first communicating channel 111 is opened to the inside space of the reservoir 101. Therefore, the inside space of the reservoir 101 is communicated with the outside space of the body-insertable apparatus by communication the second communicating channel 112 and the first communicating channel 111 with each other in the recess region 113. Because the balloon member 110 constituting the outer wall portion of the reservoir 101 is made of the elastic material such as the rubber, the balloon member 110 performs the contraction action such that the volume of the inside space of the reservoir 101 is decreased, and the fluid such as the medicine stored in the inside space of the reservoir 101 flows out to the first communicating channel 111 according to the decrease in volume. As described above, the first communicating channel 111 is communicated with the second communicating channel 112 during the releasing action. As a result, as shown in FIG. 16, the fluid flowing out from the reservoir 101 is released to the outside space of the body-insertable apparatus, i.e., the subject through the first communicating channel 111 and the second communicating channel 112.

In the releasing action, as the inside space of the reservoir 101 is decreased in association with the contraction of the balloon member 110, the volume of the air space region 116 covered with the outer surface of the balloon member 110 and the like is increased. For the increase in volume of the air space region 116, in the body-insertable apparatus according to the ninth embodiment, as shown in FIG. 16, the fluid (usually gas) flows into the air space region 116 from the control unit 104 side through the vents 114, 115, and 127, which decreases or eliminates the generation of the negative pressure according the increase in volume of the air space region 116.

Then, the advantages of the body-insertable apparatus according to the ninth embodiment will be described. The body-insertable apparatus according to the ninth embodiment has the structure in which the reservoir unit 102 and the control unit 104 are detachable. For example, the reservoir unit 102 and the control unit 104 are kept while separated from each other during the keeping, and the body-insertable apparatus is introduced in the subject while the control unit 104 is attached to the reservoir unit 102 when used. Because of the adoption of the structure in the ninth embodiment, the ninth embodiment has the advantage that the body-insertable apparatus can be realized while the running cost is reduced.

Specifically, in the body-insertable apparatus according to the ninth embodiment, the same control unit 104 can be used independently of the kinds of the medicines of which the doses are given. That is, since the reservoir unit 102 and the control unit 104 can be separated from each other, the control unit 104 can commonly be used independently of the kinds of the medicines, while it is preferable for a physician that the many reservoir units 102 are previously prepared according to the kinds of the medicines, Therefore, when the body-insertable apparatus according to the ninth embodiment is used, the preparation of the plural reservoir units 102 is enough to deal with the plural kinds of the medicines, and only the number of control units 104 according to the predicted degree of use of the body-insertable apparatus may be prepared at a maximum. Accordingly, when compared with the conventional body-insertable apparatus in which the many pieces of body-insertable apparatus are necessary to be prepared according to the kinds of the medicines, the body-insertable apparatus according to the ninth embodiment has the advantage that the number of control units 104 previously prepared can be decreased to reduce the running cost of the body-insertable apparatus. Further, since the number of control units 104 to be previously prepared can be decreased, the space for keeping the unused pieces of body-insertable apparatus can be decreased. Therefore, the body-insertable apparatus according to the ninth embodiment also has the advantage that the running cost can be decreased.

Particularly, among the components of the control mechanism 103, the shape memory member 122 is made of the shape memory alloy which is expensive compared with the usual metal materials, the control circuit 125 is formed by the predetermined electronic circuit which includes wireless function as needed, and the power unit 126 is formed by the primary battery having a predetermined capacity. Accordingly, production cost of the control unit 104 including the control mechanism 103 is usually increased when compared with the reservoir unit 102 including the balloon member 110 and the like. However, in the body-insertable apparatus according to the ninth embodiment, when compared with the conventional body-insertable apparatus, the running cost can remarkably be reduced by decreasing the number of control units 104 to be previously prepared.

Since at least the control unit 104 can repeatedly be used, from this viewpoint, the body-insertable apparatus according to the ninth embodiment has the advantage that the running cost can be reduced. As shown in FIG. 15, the control mechanism 103 included in the control unit 104 is covered with the enclosure 120 and the enclosure 105 when used, which blocks the control mechanism 103 from the outside space. Accordingly, in the control unit 104 of the ninth embodiment, the body fluid and the like never adhere to the surfaces except for the outer surface of the enclosure 120 when the body-insertable apparatus is introduced in the subject. The control unit 104 can easily be reused only by sterilization-cleaning the outer surface of the enclosure 120 after use. Therefore, when compared with the conventional technique of using the different pieces of body-insertable apparatus in each use, the body-insertable apparatus according to the ninth embodiment has the advantage that the running cost can largely be reduced.

Particularly, because the action of the control mechanism 103 is reversible, the ninth embodiment has the advantage that the reuse becomes more simply. As described above, the control mechanism 103 has the structure in which the releasing action is controlled by changing the shape of the shape memory member 122 based on the current outputted from the control circuit 125. At this point, in the shape memory member 122, the length in the longitudinal direction is contracted by the temperature rise caused by the current supply. When the current supply is stopped to decrease the temperature, the shape memory member 122 returns to the shape of the state in which the releasing action is not started yet. Accordingly, after the releasing action is finished, the length in the longitudinal direction of the shape memory member 122 becomes the same value as the state in which the releasing action is not started yet, and the position of the pressing member 121 fixed to one end of the shape memory member 122 also returns to the position of the state in which the releasing action is not started yet. Thus, in the ninth embodiment, since the actions of the components of the control mechanism 103 are reversible, it is not necessary that the physical position adjustment and the like are performed for the components of the control mechanism 103 when the control unit 104 is reused. Therefore, the ninth embodiment has the advantage that the control unit 104 can easily be reused.

Further, the body-insertable apparatus according to the ninth embodiment has the advantage that the body-insertable apparatus can be kept for a long period in the unused state. Usually the optimum storage condition of the medicine and the like stored in the reservoir 101 constituting the reservoir unit 102 does not always coincide with the optimum storage condition of the control circuit 125, the power unit 126, and the like constituting the control unit 104. On the contrary, in the body-insertable apparatus according to the ninth embodiment, since the reservoir unit 102 and the control unit 104 can independently be kept while separated from each other, each of the reservoir unit 102 and the control unit 104 can be kept on the optimum conditions concerning the temperature, the humidity, and the like. The body-insertable apparatus can be kept for a long period without degrading the function by individually keeping the reservoir unit 102 and the control unit 104 on the optimum conditions while separated. Therefore, in the body-insertable apparatus according to the ninth embodiment, the number of pieces of body-insertable apparatus disposed in the unused state can be decreased, which allows the running cost to be decreased.

The body-insertable apparatus according to the ninth embodiment adopts the configuration in which the space regions in the air space region 116 and the control unit 104 are communicated with the sheet holding substrate 108. Therefore, the fluid such as the medicine stored in the reservoir 1 can substantially completely be released into the outside space. As described above, in the ninth embodiment, since the balloon member 110 is contracted in the releasing action, the volume of the air space region 116 formed by the outer surface of the balloon member 110 and the inner surfaces of the enclosure 105 and the like is enlarged as the releasing action proceeds. Accordingly, in the case of the configuration in which the air space region 116 is blocked from other space regions, the negative pressure is generated according to the enlargement of the volume, which obstructs the contraction action of the balloon member 110.

On the contrary, the ninth embodiment adopts the configuration in which the air space region 116 is kept in the state in which the air space region 116 is communicated with other regions by forming the vents 114, 115, and 127. Therefore, as shown in FIG. 16, in accordance with the volume enlargement of the air space region 116, the fluids (gas) existing in other space regions flow into the air space region 116 through the vents 114, 115, and 127 to suppress the generation of the negative pressure in the air space region 116. As a result, the negative pressure of the air space region 116 can be inhibited from obstructing the contraction action of the balloon member 110, and the fluid such as the medicine stored in the reservoir 101 can substantially completely be released into the outside.

In the body-insertable apparatus according to the ninth embodiment, the vents 114 and 115 are formed such that the fluid in the space region in the control unit 104 flows into the air space region 116, which also gives the advantage. That is, in order to suppress the generation of the negative pressure in the air space region 116, for example the air space region 116 and the outside space may be configured to be communicated with each other by forming the vent in the enclosure 105. However, in this case, the body fluid and the like existing in the outside space, i.e., the subject flows into the body-insertable apparatus.

As described above, in the ninth embodiment, at least the control unit 104 is reused. From the viewpoint of easy reuse of the control unit 104, it is necessary to adopt the configuration in which the fluid such as the body fluid flowing into the air space region 116 is prevented from flowing into the control unit 104. Therefore, when the vent is formed in the enclosure 5, it is obvious to adopt the configuration in which the vents 114 and 115 are neglected. Further, for example, not only it is necessary that the sheet holding substrate 108 is formed by the watertight member, but also it is necessary to adopt the watertight configuration in the contact portion between the side face of the end portion of the sheet holding substrate 108 and the inner surface of the enclosure 105. Therefore, there is possibility that the production cost of the reservoir unit 102 is increased. On the contrary, the ninth embodiment adopts the configuration in which the air space region 116 is communicated not with the outside space, but with the space region in the control unit 104, so that it is not necessary to adopt the complicated structure having the watertight sheet holding substrate 108 and the like. Therefore, the ninth embodiment has the advantage that the production cost can be prevented from increasing.

The configuration in which the sheet member 107 and the pressing member 121 are always fixed and brought into close contact with each other may be adopted in the ninth embodiment. Specifically, for example, the pressing member 121 and the sheet member 107 can integrally be moved by arranging the adhesive material such as an adhesive sheet in the contact surface between the sheet member 107 and the pressing member 121. In this case, the cavity portion is securely generated between the sheet member 107 and the sheet holding substrate 108 when the pressing member 121 is moved toward the direction in which the pressing member 121 is separated away from the sheet holding substrate 108 according to the change in shape of the shape memory member 122. Therefore, assuredness is improved in the communication state between the first communicating channel 111 and the second communicating channel 112.

Modification

Then, a modification of the body-insertable apparatus according to the ninth embodiment will be described. Although the modification is substantially equal to the ninth embodiment with respect to the structure of the body-insertable apparatus, the design in which the in-flow and out-flow of the fluid are suppressed more effectively when the reservoir unit 102 is separated from the control unit 104 is performed with respect to the reservoir unit 102 in the modification.

Figure 17:
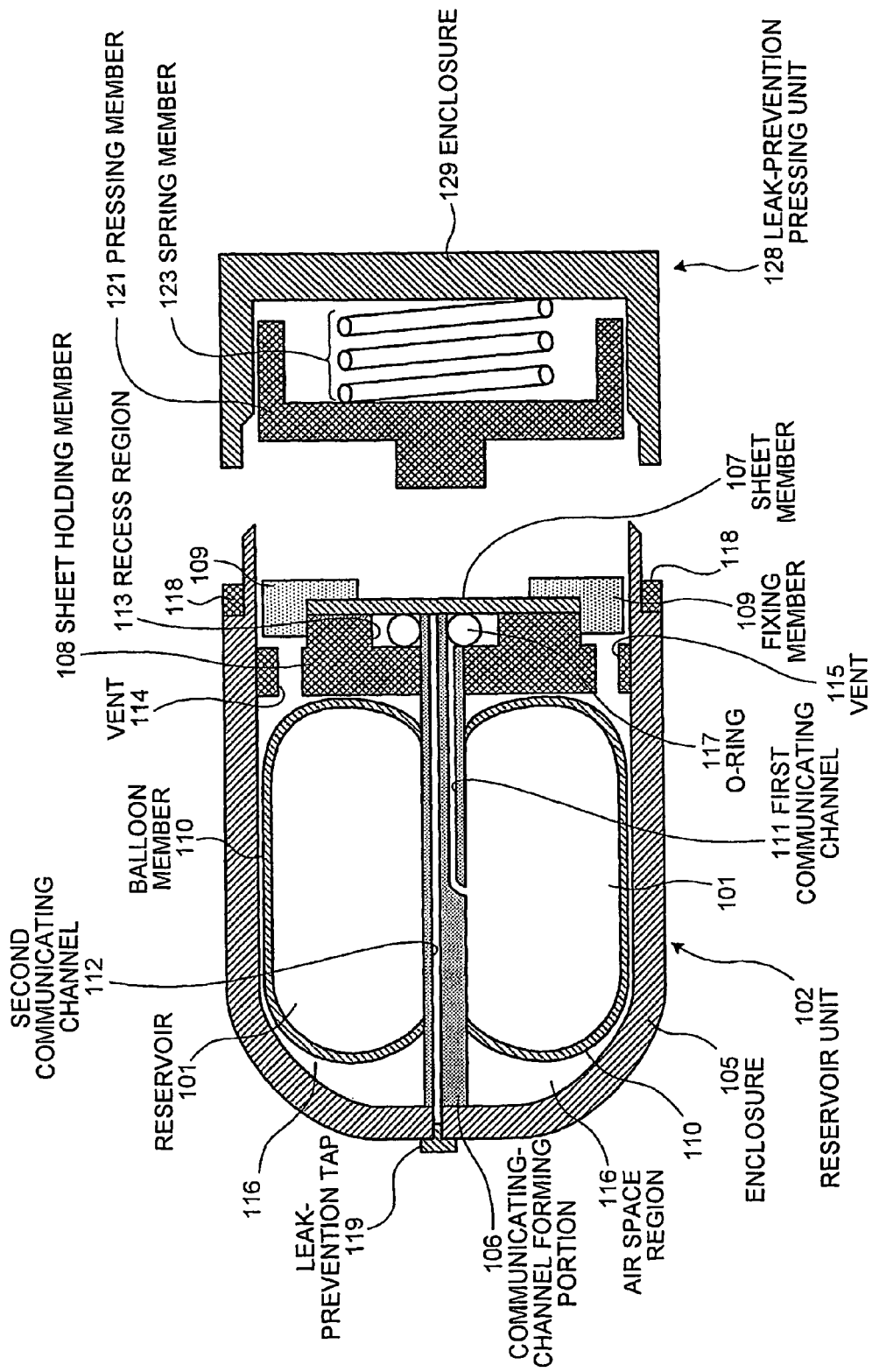
FIG. 17 is a schematic view for explaining an action of a body-insertable apparatus according to a modification of the ninth embodiment.

FIG. 17 is a schematic view showing the reservoir unit 102 and a leak-prevention pressing unit 128 attached to the reservoir unit 102 in the keeping of the reservoir unit 102. As shown in FIG. 17, the leak-prevention pressing unit 128 has the configuration in which the shape memory member 122, the control circuit 125, and the power unit 126 are neglected from the control unit 104. The leak-prevention pressing unit 128 has the configuration in which the pressing force is continuously applied to the sheet member 107 when the reservoir unit 102 is attached. Specifically the leak-prevention pressing unit 128 includes an enclosure 129, the pressing member 121, and the spring member 123. In the enclosure 129, a portion to which the reservoir unit 102 is attached is opened. The pressing member 121 applies the pressing force to the sheet member 107 toward the direction in which the sheet member 107 is brought close to the sheet holding substrate 108 when the leak-prevention pressing unit 128 is attached to the reservoir unit 102. The spring member 123 biases the snapping force to the pressing member 121. As with the control unit 104, the enclosure 129 has the outer diameter about the central axis in the longitudinal direction of the reservoir unit 102 (crosswise direction in FIG. 17), and the outer diameter of the enclosure 129 is substantially equal to the reservoir unit 102. The enclosure 129 has the structures in which the enclosure 129 is attachable to the reservoir unit 102 in the mechanical manner such as the screw-thread method or the machine-screw method.

Then, in the modification, the advantage obtained by including the leak-prevention pressing unit 128 will be described. As shown in FIG. 17, the leak-prevention pressing unit 128 has substantially the same structure as the control unit 104 with respect to the structure near the portion where the leak-prevention pressing unit 128 is attached to the reservoir unit 102. Accordingly, when the reservoir unit 102 is kept in a storage room and the like while separated from the control unit 104, the reservoir unit 102 is kept in the same state as the state, in which the control unit 104 is attached, by attaching the leak-prevention pressing unit 128 to the reservoir unit 102. Therefore, in addition to the action of the leak-prevention tap 119, the leakage of the fluid can be prevented more securely. The modification has the advantages that not only the body-insertable apparatus can be kept for a long period but also the leakage of the fluid can be securely prevented against vibration generated during transport.

Tenth Embodiment

Figure 18:
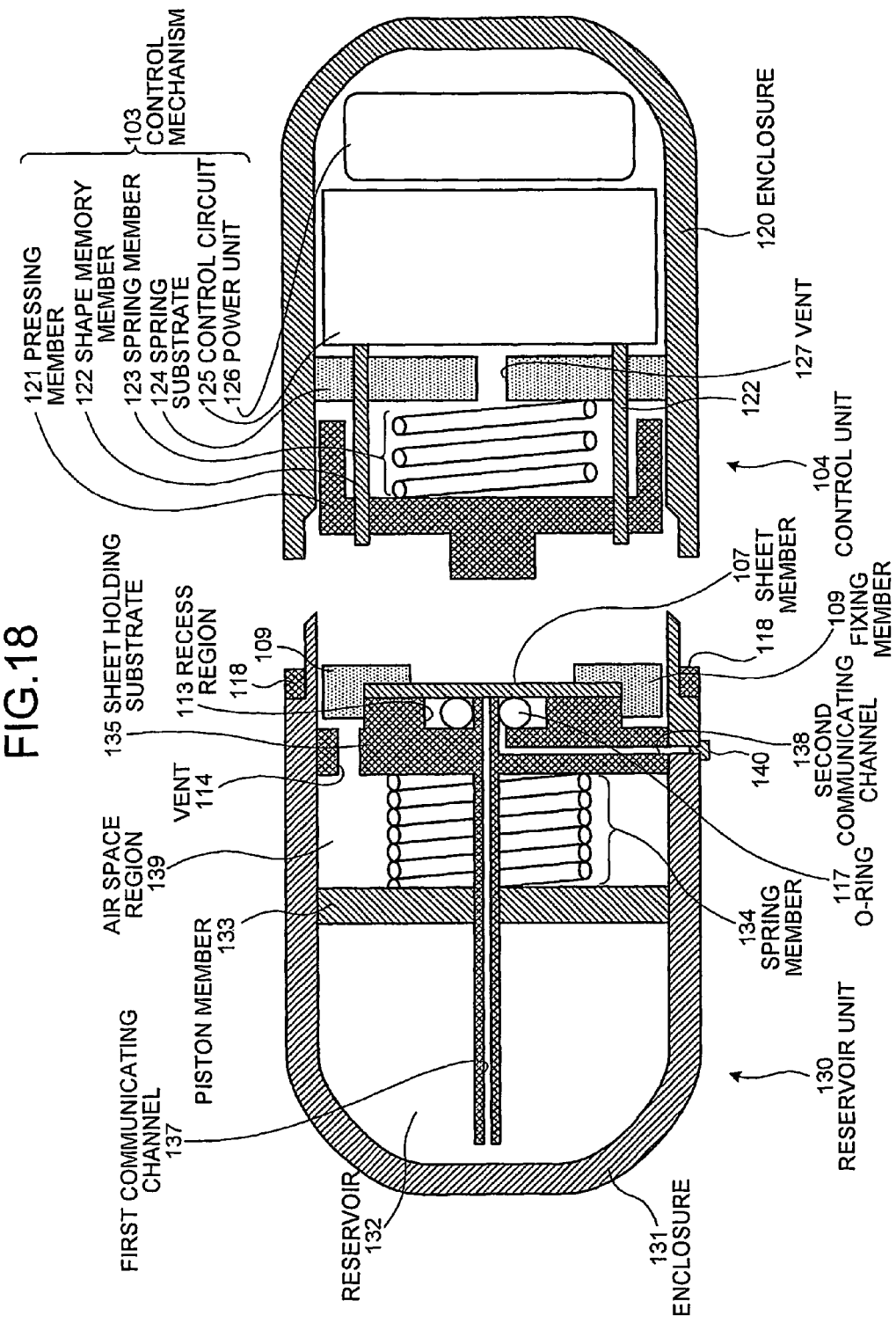
FIG. 18 is a schematic view showing a body-insertable apparatus according to a tenth embodiment while the body-insertable apparatus is divided into units.

Then, a body-insertable apparatus according to a tenth embodiment will be described. FIG. 18 is a schematic view showing the body-insertable apparatus according to the tenth embodiment while the body-insertable apparatus is divided into the units. As shown in FIG. 18, the body-insertable apparatus according to the tenth embodiment has the configuration in which a reservoir unit 130 differs from the reservoir unit 102 in the ninth embodiment. In the tenth embodiment, the component designated by the same name and numeral as the ninth embodiment shall has the same structure and function as the ninth embodiment unless otherwise stated. That is also true of the later-mentioned descriptions of eleventh and twelfth embodiments.

As shown in FIG. 18, the reservoir unit 130 includes an enclosure 131 and components arranged in the enclosure 131. The enclosure 131 has an opening in the portion to which the control unit 104 is attached. Specifically the inside of the enclosure 131 includes a piston member 133, a spring member 134, and a sheet holding substrate 135. The piston member 133 is movably arranged in the longitudinal direction (horizontal direction in FIG. 18) of the body-insertable apparatus, and the piston member 133 constitutes a part of the outer wall portion of a reservoir 132 along with a part of the enclosure 131. The spring member 134 biases the snapping force to the piston member 133. The sheet holding substrate 135 fixes the spring member 134, and the sheet holding substrate 135 holds the sheet member 107.

The piston member 133 forms a part of the outer wall portion of the reservoir 132, and the piston member 133 has the function of releasing the fluid to the outside space by the movement of the piston member 133 toward the direction in which the volume of the inside space of the reservoir 132 is decreased in the fluid releasing action. Specifically, in the configuration, the piston member 133 is formed by a plate-shape body arranged movable in the longitudinal direction while the end portion abuts on the inner surface of the side face in the longitudinal direction of the enclosure 131, and the piston member 133 is moved toward the direction in which the volume of the inside space in the reservoir 132 is decreased based on the snapping force applied by the spring member 134.

The spring member 134 is one which biases the snapping force to the piston member 133. Specifically, the spring member 134 is arranged in an air space region 139 which is of the space region between the sheet holding substrate 135 and the piston member 133, the end portion of the spring member 134 is fixed to both the piston member 133 and the sheet holding substrate 135, and the spring member 134 is arranged while compressed shorter than the natural length. The spring member 134 has the function of biasing the snapping force to the piston member 133 toward the direction in which the volume of the reservoir 132 is decreased, i.e., leftward in FIG. 18.

Similarly to the sheet holding substrate 108 in the ninth embodiment, in the structure of the sheet holding substrate 135, the recess region 113 is formed, the sheet holding substrate 135 has the function of holding the sheet member 107 which is arranged such that the recess region 113 is covered with the sheet member 107, and the vent 114 is formed. The sheet holding substrate 135 also has the function as the communicating channel forming portion. Specifically the sheet holding substrate 135 has the structure in which a first communicating channel 137 and a second communicating channel 138 are formed. The first communicating channel 137 is extended in the longitudinal direction of the body-insertable apparatus, and one end of the first communicating channel 137 is opened to the inside space of the reservoir 132 while the other end is opened to the recess region 113. The second communicating channel 138 is mainly extended in the direction perpendicular to the longitudinal direction of the body-insertable apparatus, and one end of the second communicating channel 138 is opened to the recess region 113 while the other end is opened to the outside space. As shown in FIG. 18, in the state in which the reservoir unit 130 and the control unit 104 are separated from each other, in order to prevent the leakage of the fluid stored in the reservoir 132 to the outside space, the reservoir unit 130 is kept while a leak-prevention tap 140 is inserted into the end portion, opened to the outside space, of the second communicating channel 138. The separate rod-shaped member different from the sheet holding substrate 135 may be used as the member constituting the first communicating channel 137.

In the tenth embodiment, an attachment mode of the control unit 104 to the reservoir unit 130 is similar to the attachment mode between the reservoir unit 102 and the control unit 104 in the ninth embodiment. Specifically, the outer diameters about the central axis in longitudinal direction are substantially similar to each other in the enclosure 131 constituting the reservoir unit 130 and the enclosure 120 constituting the control unit 104, and one of the enclosure 131 and the enclosure 120 can be attached to the other, for example, in the mechanical manner such as the screw-thread method or the machine-screw method. In the state in which the control unit 104 is attached to the reservoir unit 130, the watertight rubber member 118 is arranged between the enclosure 131 and the enclosure 120, and the fluid is prevented from invading from the outside space through the coupling portion between the enclosure 131 and the enclosure 120.

Then, the action of the body-insertable apparatus according to the tenth embodiment will briefly be described. In the tenth embodiment, the control unit 104 has the same configuration as the ninth embodiment. Before the releasing action is performed, while the pressing member 121 abuts onto the sheet member 107, the pressing member 121 blocks the communication state between the first communicating channel 137 and the second communicating channel 138 by applying the predetermined pressing force. On the other hand, when the releasing action is performed, the position of the pressing member 121 is changed based on the current outputted from the control circuit 125, and the pressing force applied to the sheet member 107 is decreased or eliminated. Therefore, the close contact state between the sheet member 107 and the end portion of the first communicating channel 137 is released to communicate the first communicating channel 137 and the second communicating channel 138 with each other in the recess region 113.

As described above, the other end of the first communicating channel 137 is opened to the inside space of the reservoir 132, and the other end of the second communicating channel 138 is opened to the outside space. Therefore, the inside space of the reservoir 132 and the outside space of the body-insertable apparatus are communicated with each other by communicating the first communicating channel 137 and the second communicating channel 138 with each other in the recess region 113. At this point, the piston member 133 is moved by the action of the spring member 134 toward the direction in which the volume of the inside space of the reservoir 132 is decreased, which allows the fluid stored in the reservoir 132 to be pushed out to the outside space through the first communicating channel 137 and the second communicating channel 138.

Then, the advantages of the body-insertable apparatus according to the tenth embodiment will be described. First the body-insertable apparatus according to the tenth embodiment has the configuration in which the control unit 104 is detachable from the reservoir unit 130, and the structure of the control unit 104 is similar to the ninth embodiment, so that the tenth embodiment can obtain the same advantages described in the ninth embodiment with respect to the control unit.

Similarly to the reservoir unit 102 in the ninth embodiment, in the body-insertable apparatus according to the tenth embodiment, the volume of the air space region 139 is increased according to the decrease in volume of the reservoir 132 in the fluid releasing action, and the reservoir unit 130 has the configuration in which the air space region 139 and the space region of the control unit 104 are communicated through the vent 114. Accordingly, similarly to the ninth embodiment, the body-insertable apparatus according to the tenth embodiment has the advantages that the body fluid and the like do not flow into the inside from the outside space and the like.

Eleventh Embodiment

Then, a body-insertable apparatus according to an eleventh embodiment will be described. In the configuration of the body-insertable apparatus according to the eleventh embodiment, the control unit includes a pump mechanism which is of a part of the control mechanism, and the fluid the releasing action is performed by the action of the pump mechanism.

Figure 19:
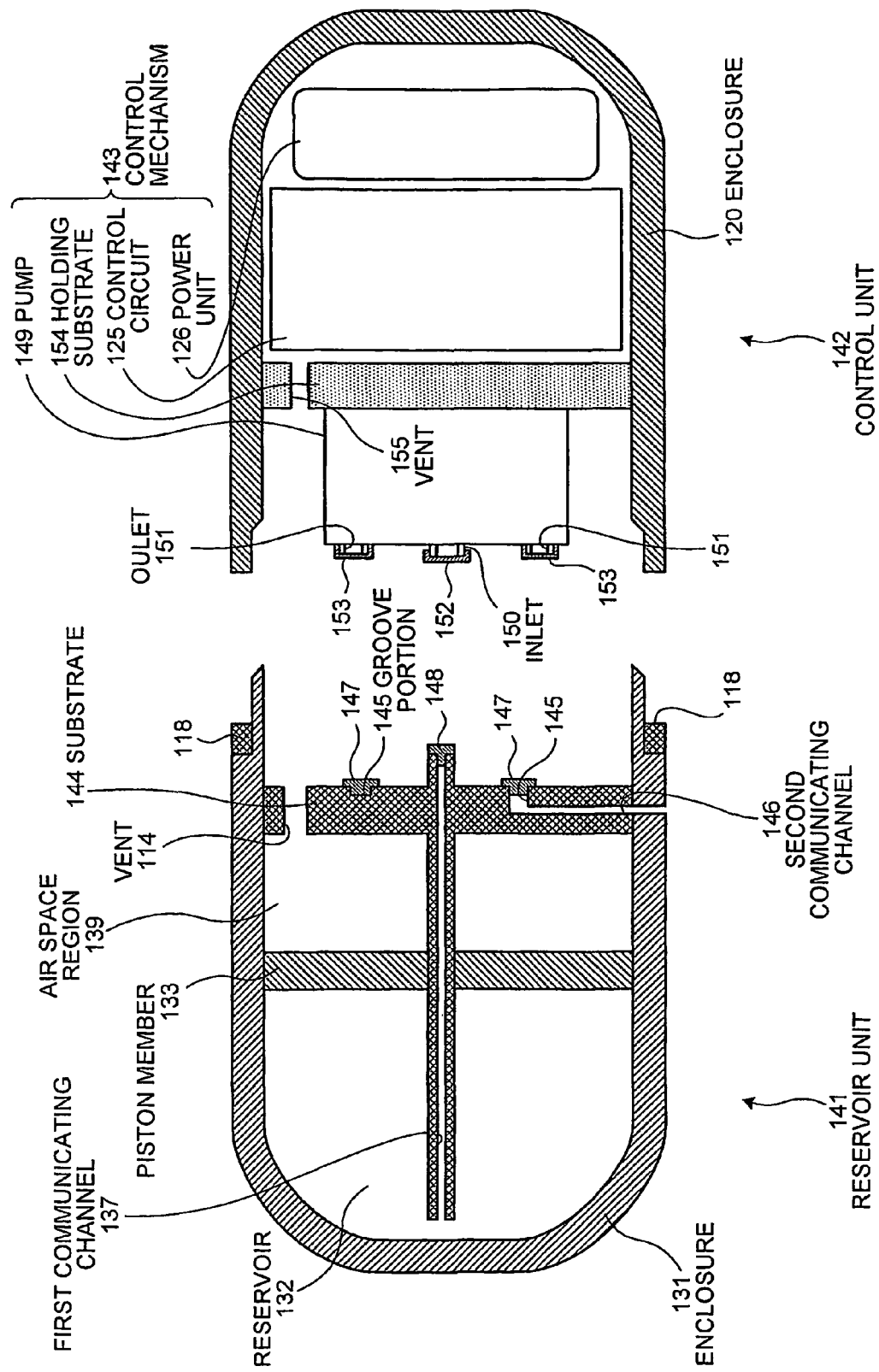
FIG. 19 is a schematic view showing a body-insertable apparatus according to an eleventh embodiment while the body-insertable apparatus is divided into units.

FIG. 19 is a schematic view showing the body-insertable apparatus according to the eleventh embodiment while the body-insertable apparatus is divided into the units. As shown in FIG. 19, the body-insertable apparatus according to the eleventh embodiment is formed by a reservoir unit 141 and a control unit 142 which is formed so as to be detachable from the reservoir unit 141. Compared with the tenth embodiment, while the reservoir unit 141 has the configuration in which the spring member 134 is neglected, a control mechanism 143 included in the control unit 142 has a pump 149 which releases the fluid to the outside space.

Specifically, as with the tenth embodiment, the reservoir unit 141 includes the reservoir 132 and the piston member 133 inside the enclosure 131. The reservoir unit 141 newly includes a substrate 144 instead of the sheet holding substrate 135. The substrate 144 has the same structure as the sheet holding substrate 135 in that the vent 114, the first communicating channel 137, and a second communicating channel 146 are formed. However, in the structure of the substrate 144, the recess region 113 is not formed, and one end the first communicating channel 137 and one end the second communicating channel 146 are opened in the surface (surface on the side to which the control unit 142 is attached) of the substrate 144. More specifically, in the surface of the substrate 144, an annular groove portion 145 whose center is set at the central axis in the longitudinal direction of the body-insertable apparatus is formed in order to be communicated with an outlet 151 (described later) of the pump 149, and the second communicating channel 146 is formed so as to be communicated with the surface side of the substrate 144 through the groove portion 145. The reservoir unit 141 has the configuration in which leak-prevention taps 147 and 148 are inserted into the groove portions 145 and the end portion of the first communicating channel 137 respectively. At this point, the leak-prevention tap 147 blocks the communication between the surface side of the substrate 144 and the outside space in the second communicating channel 146. The leak-prevention tap 148 prevents the leakage of the fluid held by the reservoir 132 when the reservoir unit 141 is separated from the control unit 142.

In addition to the power unit 126 and the control circuit 125, the control unit 142 includes the pump 149 and a holding substrate 154 as the control mechanism 143. The holding substrate 154 holds the pump 149. In the eleventh embodiment, the power unit 126 has the configuration in which the drive power is supplied not only to the control circuit 125 but the pump 149, and the control circuit 125 controls the drive state of the pump 149. A vent 155 is formed in the holding substrate 154. Similarly to the vent 127 in the ninth embodiment and the like, the vent has the function of causing the fluid, located in the space region where the control circuit 125 and the like are arranged, to flow into the air space region 139 when the control unit 142 is attached to the reservoir unit 141.

The pump 149 includes an inlet 150 for sucking the fluid and the outlet 151 for releasing the fluid. In the eleventh embodiment, the outlet 151 has the annular shape whose center is set at the central axis in the longitudinal direction of the body-insertable apparatus corresponding to the groove portion 145 formed in the reservoir unit 141, and the inlet 150 is formed so as to be located at the central axis in the longitudinal direction of body-insertable apparatus corresponding to the first communicating channel 137. Since the outlet 151 and the inlet 150 have the above configurations, when the control unit 142 is attached to the reservoir unit 141, the outlet 151 is fitted in the groove portion 145 and the inlet 150 is fitted in the end portion of the first communicating channel 137. When the control unit 142 is separated from the reservoir unit 141, in order to protect the inlet 150 and the outlet 151, the pump 149 has the configuration in which protective taps 152 and 153 are fitted in the inlet 150 and the outlet 151 respectively.

The attachment mode of the control unit 142 to the reservoir unit 141 is basically similar to the ninth embodiment and the like. However, in the body-insertable apparatus according to the eleventh embodiment, the leak-prevention taps 147 and 148 and the protective taps 152 and 153 are arranged not in the outer surfaces of the enclosure 131 and the like, but in the region which becomes the inside of the body-insertable apparatus. Therefore, before the control unit 142 is attached to the reservoir unit 141, the leak-prevention tap 147 and the like are detached from the groove portion 145 and the like, and then the control unit 142 is attached to the reservoir unit 141 by the thread connection or the like.

Then, the action of the body-insertable apparatus according to the eleventh embodiment will briefly be described. In the body-insertable apparatus which is introduced in the subject while the control unit 142 is attached to the reservoir unit 141, when the body-insertable apparatus reaches a predetermined region in the subject, the control circuit 125 performs the predetermined control, e.g., performs the current supply to piston member 133 such that the fluid the releasing action is performed. The drive of the pump 149 is started based on the control, and the pump 149 performs the pump action in which the inputted fluid is released again through the outlet 151 while the fluid is inputted through the inlet 150. As described above, when the control unit 142 is attached to the reservoir unit 141, the inlet 150 is fitted in the first communicating channel 137 and the outlet 151 is fitted in the groove portion 145. Therefore, by starting the drive of the pump 149, the fluid such as the medicine stored in the reservoir 132 is temporarily inputted to the pump 149 through the first communicating channel 137 and the inlet 150, and the fluid is released into the outside space through the outlet 151, the groove portion 145, and the second communicating channel 146. Since the piston member 133 is moved toward the direction in which the volume of the inside space of the reservoir 132 is decreased in association with the release of the fluid stored in the reservoir 132 to the outside, the volume of the air space region 139 is increased. The vent 114 and the vent 155 function according to the increase in volume. Specifically the fluids existing space regions in the control unit 142 flows into the air space region 139 through the vent 155 and the vent 114, which prevents the generation of the negative pressure caused by the increase in volume in the air space region 139.

Thus, even if the configuration in which the control mechanism 143 includes the pump 149 is adopted, the advantages of the invention described in the ninth and tenth embodiments can be obtained by the configuration in which the reservoir unit 141 and the control unit 142 are detachable to each other. Particularly, usually the pump 149 is expensive when compared with other components, so that the running cost can remarkably be decreased by reusing the control mechanism 143 including the pump 149.

Modification

Figure 20:
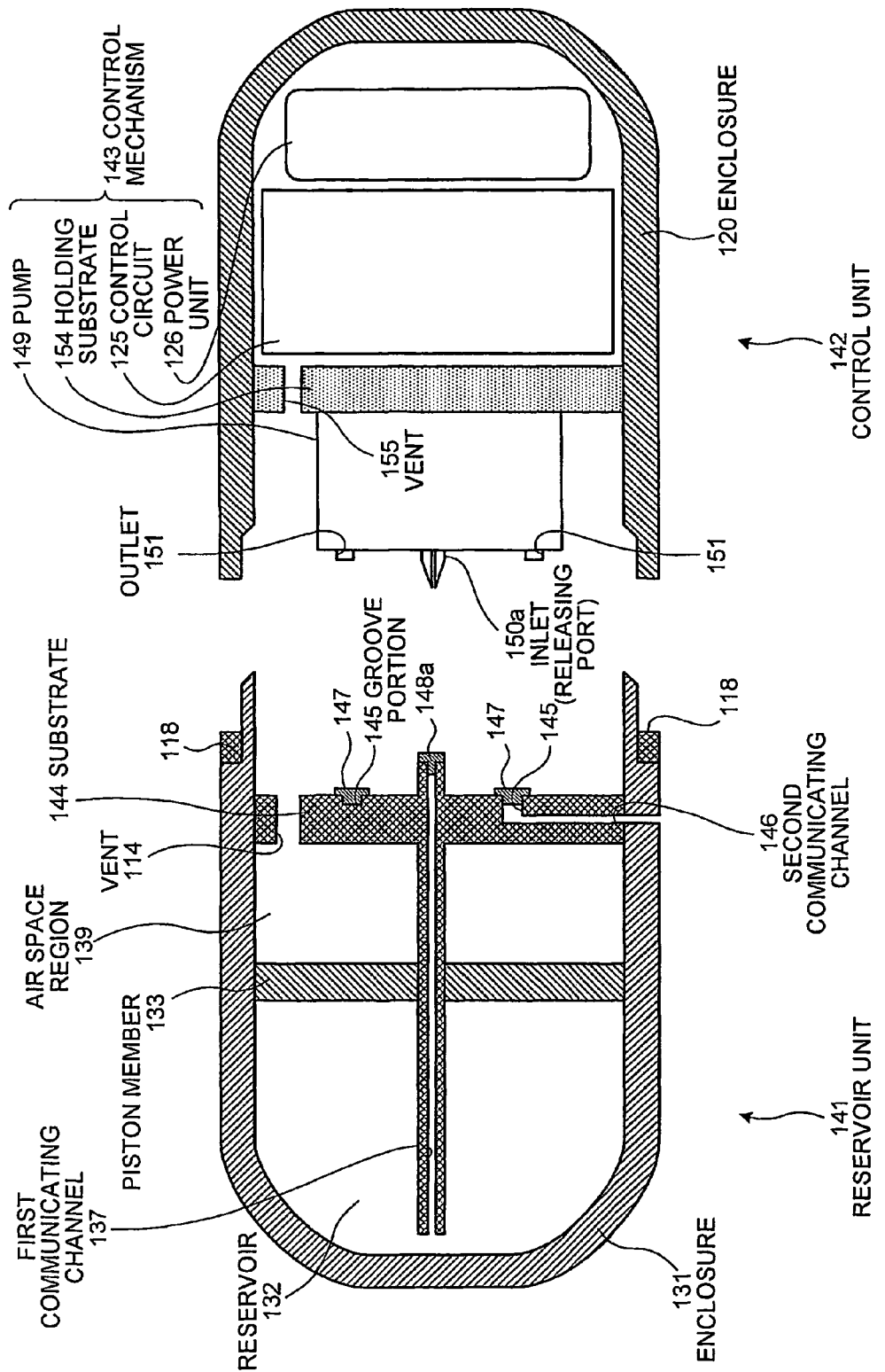
FIG. 20 is a schematic view for explaining a body-insertable apparatus according to a modification of the eleventh embodiment.

Then, a modification of the body-insertable apparatus according to the eleventh embodiment will be described. FIG. 20 is a schematic view showing the body-insertable apparatus according to the modification. As shown in FIG. 20, the body-insertable apparatus according to the modification includes an inlet 150a and a leak-prevention tap 148a. The inlet 150a has a sharpened shape at a leading end portion, where the inlet 150a comes into contact with the first communicating channel 137, and the inlet 150a is arranged instead of the inlet 150 in the eleventh embodiment. The leak-prevention tap 148a is used instead of the leak-prevention tap 148, and the leak-prevention tap 148a is fixed to the opening on the control unit side of the first communicating channel 137.

Not only the inlet 150a has the function of inputting the fluid stored in the reservoir 132 to the pump 149 through the first communicating channel 137, but also the inlet 150a functions as a releasing port for releasing the leak-prevention tap 148a when the control unit 142 is attached to the reservoir unit 141. Specifically, as shown in FIG. 20, the inlet 150a whose leading end portion is sharpened, and the inlet 150a has the function of communicating the first communicating channel 137 and the pump 149 with each other by entering the leak-prevention tap 148a when the leading end portion is in contact with the leak-prevention tap 148a. In accordance with the arrangement of the inlet 150a, the leak-prevention tap 148a is arranged while fixed to the first communicating channel 137, and the leak-prevention tap 148a is formed by the member which is entered when the inlet 150a comes into contact with the leak-prevention tap 148a while serving the leakage prevention function.

Thus, in the modification, when the control unit 142 is attached to the reservoir unit 141, the inlet 150a and the first communicating channel 137 can be communicated with each other without previously taking off the leak-prevention tap 148a. In the configuration shown in FIG. 20, although the same configuration as the eleventh embodiment is employed with respect to the outlet 151 and the leak-prevention tap 147. However, the outlet 151 may be formed in the sharpened structure like the inlet 150a, and the leak-prevention tap 147 may be fixed to the groove portion 145 and formed by the member that can be opened similar to the leak-prevention tap 148a.

The leak-prevention tap 147 can also be neglected. Even if the leak-prevention tap 147 is neglected, it is obvious that the separation of the reservoir unit 141 from the control unit 142 does not have an adverse influence on the leakage prevention of the fluid held in the reservoir 132.

Twelfth Embodiment

Then, a body-insertable apparatus according to a twelfth embodiment will be described. The pieces of body-insertable apparatus according to the ninth to eleventh embodiments are one which releases the fluid such as the medicine previously stored in the reservoir into the outside space. On the other hand, the body-insertable apparatus according to the twelfth embodiment is one which takes in the fluid such as the body fluid of the subject from the outside space into the reservoir using a predetermined mechanism. In the body-insertable apparatus used for the purpose of the twelfth embodiment, the direction the fluid is moved is in the opposite direction to the fluid direction of the pieces of body-insertable apparatus according to the ninth to eleventh embodiments, so that the body-insertable apparatus according to the twelfth embodiment can be realized by diverting the mechanisms of the pieces of body-insertable apparatus according to the ninth to eleventh embodiments. An example in which the body-insertable apparatus according to the second embodiment is employed will be described below. However, it is obvious that the body-insertable apparatus which takes in the fluid such as the body fluid from the outside space can be realized by employing the ninth to eleventh embodiments.

Figure 21:
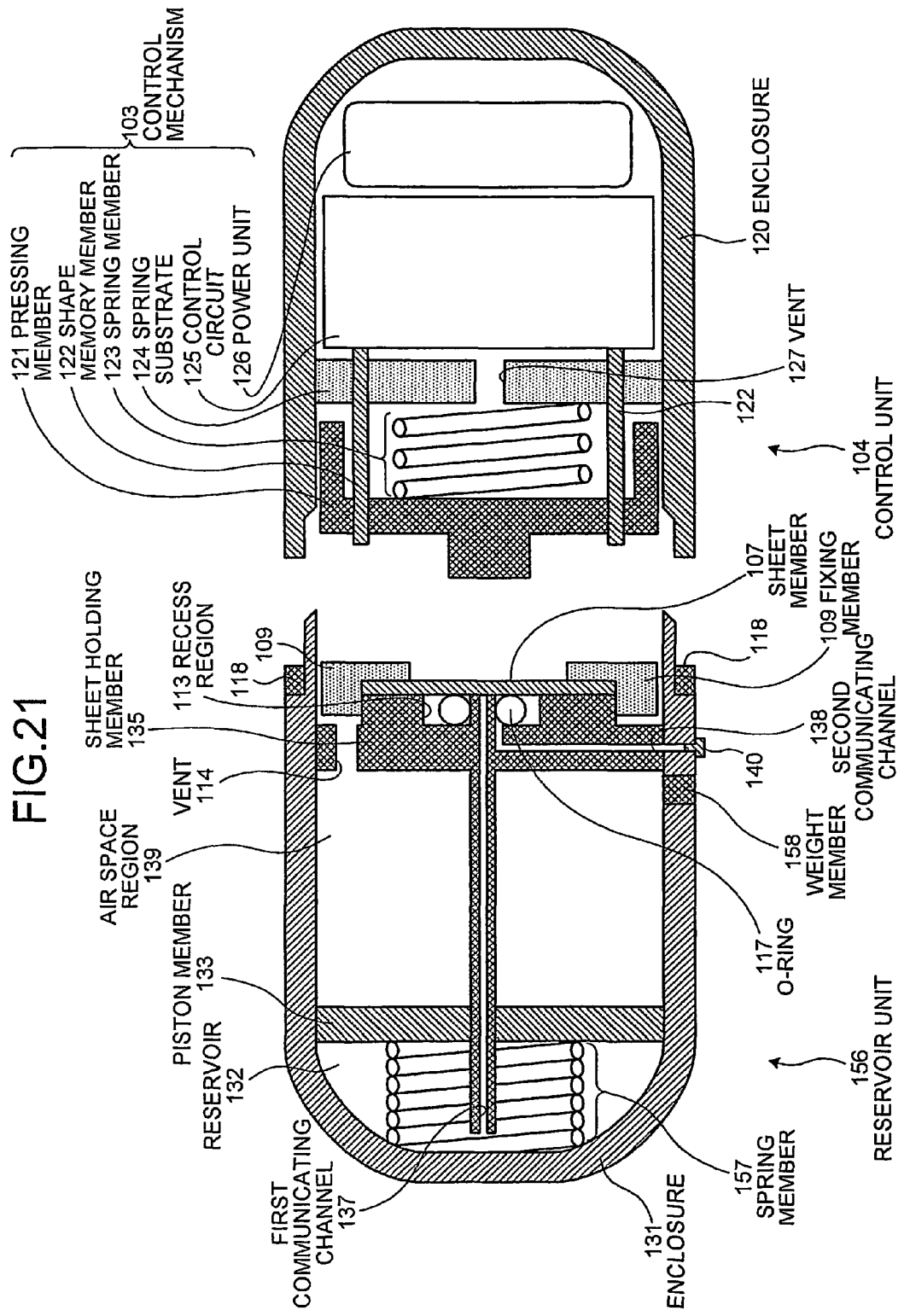
FIG. 21 is a schematic view showing a body-insertable apparatus according to a twelfth embodiment while the body-insertable apparatus is divided into units.

FIG. 21 is a schematic view showing the body-insertable apparatus according to the twelfth embodiment while the body-insertable apparatus is divided into the units. As shown in FIG. 21, while the body-insertable apparatus according to the twelfth embodiment substantially has the same configuration as the body-insertable apparatus according to the tenth embodiment, the body-insertable apparatus according to the twelfth embodiment has the configuration in which a spring member 157 is used in a reservoir unit 156 instead of the spring member 134 in the tenth embodiment.

Specifically the reservoir unit 156 includes a spring member 157. The spring member 157 is arranged not between the piston member 133 and the sheet holding substrate 135, but on the side of the piston member 133 which is opposite the sheet holding substrate 135, i.e., the left side in FIG. 21 while compressed shorter than the natural length. The spring member 157 has the function of biasing the snapping force to the piston member 133 toward the direction in which the piston member 133 is brought close to the sheet holding substrate 135, i.e., in the direction in which the volume of the inside space of the reservoir 132 is increased.

The reservoir unit 156 has the configuration in which a weight member 158 is arranged in a part of the enclosure 131 and near the opening of the second communicating channel 138 to the outside space. For example, the weight member 158 is formed by the member whose specific gravity is larger than that of the member constituting the enclosure 131, and the weight member 158 acts such that the opening of the second communicating channel 138 to the outside space is orientated downward in the vertical direction. The configuration which realizes the action is not limited to the case in which the weight member 158 is provided. For example, the arrangement of the components may be devised such that the center of gravity of the entire body-insertable apparatus is located near the opening of the second communicating channel 138 to the outside space. From the viewpoint of dynamics, such the structure can be regarded as the case in which the weight member 158 is provided, and the opening of the second communicating channel 138 to the outside space is orientated downward in the vertical direction.

The action of the body-insertable apparatus according to the twelfth embodiment will be described below. First, similarly to the tenth embodiment, the close contact state between the sheet member 107 and the end portion of the first communicating channel 137 is released by the function of the control unit 104, and the inside space of the reservoir 132 is communicated with the outside space through the first communicating channel 137 and the second communicating channel 138.

Then, the piston member 133 is moved toward the direction of the sheet holding substrate 135 to increase the volume of the reservoir 132 by the function of the spring member 157. The negative pressure is generated in the inside space of the reservoir 132 according to the increase in volume. The fluid existing in the outside space, communicated with the inside space of the reservoir 132, of the body-insertable apparatus flows into the inside space of the reservoir 132 through the second communicating channel 138 and the first communicating channel 137. Thus, the fluid such as the body fluid is taken in the reservoir 132.

In not only the body-insertable apparatus having the fluid releasing function but the body-insertable apparatus having the fluid sampling function like the twelfth embodiment, it is useful to adopt the configuration in which the reservoir unit 156 and the control unit 104 are detachable. As can be seen from comparison of FIG. 18 and FIG. 21, in the body-insertable apparatus according to the twelfth embodiment, the running cost can be reduced by adopting the detachable configuration.

In the body-insertable apparatus for sampling the fluid, it is also useful to provide the vent 114. In the twelfth embodiment, in performing the fluid sampling action, as described above, the volume of the reservoir 132 is changed (increased), and the volume of the air space region 139 is decreased according to the change in volume. Therefore, when the vent 114 is not provided, the air in the air space region 139 is compressed according to the decrease in volume to increase the pressure inside the air space region 139, which possibly obstructs the movement of the piston member 133 toward the sheet holding substrate 135. On the contrary, in the twelfth embodiment, since the vent 114 is formed in the sheet holding substrate 135, the air space region 139 keeps the communicated state between the air space region 139 and the space region in the control unit 104. Therefore, the pressure rise can be relieved in the air space region 139, the obstruction of the movement of the piston member 133 can be suppressed, and the prevention of the fluid sampling action can be suppressed.

Thus, in the body-insertable apparatus for sampling the body fluid and the like in the outside space like the body-insertable apparatus according to the twelfth embodiment, the same advantages as the body-insertable apparatus for releasing the fluid such as the medicine described in the ninth to twelfth embodiments can be obtained. That is, in the body-insertable apparatus of the invention, the reservoir unit including the reservoir in which the predetermined fluid is stored and the control unit including the control mechanism which controls the action timing for the reservoir concerning at least one of the input and output of the fluid adopt the structure in which the reservoir unit and the control unit are detachable. It is not necessary that the scope of the invention is limited to the body-insertable apparatus for releasing the fluid such as the medicine to the outside. It is possible that not only one of the fluid the releasing action and the fluid sampling action is performed, but also both the fluid the releasing action and the fluid sampling action are performed. For example, in the twelfth embodiment, the pump 149 may be used so as to be able to reverse the fluid moving direction (namely, the fluid inputted through the outlet 151 is outputted through the inlet 150). In the body-insertable apparatus according to the ninth embodiment, the vents 114 and 115 are neglected, a through hole is made in a part of the enclosure 105, and the sampled fluid may be stored in the air space region 116.

As shown in FIG. 21, the body-insertable apparatus according to the twelfth embodiment has the structure in which the weight member 158 is arranged near the opening of the second communicating channel 138 to the outside space. When the weight member 158 is arranged near the opening of the second communicating channel 138, the body-insertable apparatus according to the twelfth embodiment can be kept in the state in which the opening of the second communicating channel 138 is orientated downward in the vertical direction by the action of the weight member 158 in the subject. At this point, usually the body-insertable apparatus is moved while being in contact with the portion located downward in the vertical direction for the body-insertable apparatus in the inner wall of the digestive system which is of the passage, so that the body-insertable apparatus according to the twelfth embodiment can perform the fluid sampling action to the inner wall of the digestive system where the body fluid and the like exist richly by maintaining the state in which the opening of the second communicating channel 138 is orientated downward in the vertical direction.

Thus, the ninth to twelfth embodiments of the invention are described. The invention shall not be limited to the above embodiments, and those skilled in the art could make various embodiments and modifications. For example, any control mechanism can be used as long as the control mechanism can control the input action and/or the output action of the predetermined fluid such as the medicine and the body fluid, and it is not necessary that the control mechanism is not limited to the control mechanism 103 and the like shown in FIG. 14 and the like. Specifically, as shown in the ninth and tenth embodiments, the control mechanism may be one which controls the input and output timing of the fluid. Further, as shown in the eleventh embodiment, the control mechanism may be one in which not only the input and output timing is controlled but also the pump for generating the flow state of the fluid is included.

In the ninth to twelfth embodiments, the leak-prevention tap blocks the communication state between the outside space and the second communicating channel or the like. However, the leak-prevention tap may have the function of preventing the leakage of the fluid stored in the reservoir to the outside. Accordingly, a check valve which can move the fluid from the outside space toward the reservoir while preventing the movement of the fluid from the reservoir toward the outside space may be adopted as the leak-prevention tap. In this case, for example, when the fluid such as the medicine is previously injected into the reservoir before use, the body-insertable apparatus has the advantages that the leakage of the fluid which is injected once can be prevented by inserting the leak-prevention tap while the fluid can be injected even if the leak-prevention tap is inserted.

Further, the weight member 158 in the twelfth embodiment may be arranged near the opening of the second communicating channel to the outside space in the ninth to eleventh embodiments. In this case, there is the advantage that the fluid such as the medicine stored in the reservoir can securely be released into the inner wall portion of the digestive system. The weight member 158 is not arranged at the predetermined position, but the center of gravity of the entire body-insertable apparatus is configured to be located near the opening of the second communicating channel to the outside space, which also allows the opening to be orientated downward in the vertical direction.

Note 1

A method of assembling a body-insertable apparatus including a reservoir unit having a reservoir in which a predetermined fluid is stored; and a communicating channel (for example, the first communicating channel in the first embodiment) in which one end is opened to an outside space of the body-insertable apparatus, the communicating channel being able to communicate the reservoir and the outside space, a control mechanism which controls a communication state between the reservoir and the outside space in the communicating channel, and a control unit which is formed to be detachable from the reservoir unit, the body-insertable apparatus assembling method characterized by including an attaching process of attaching the control unit to the reservoir unit, and an opening process of taking off a leak-prevention tap inserted into the opening of the communicating channel to the outside space after the control unit is attached.

Note 2

A method of assembling a body-insertable apparatus including a reservoir unit having a reservoir in which a predetermined fluid is stored; and a communicating channel (for example, the first communicating channel in the third embodiment) in which one end is opened to an inside of the reservoir while the other end is opened to an inside of the body-insertable apparatus, the communicating channel forming at least a part of a passage of the predetermined fluid when input and/or output of the predetermined fluid is performed between the reservoir and an outside space of the body-insertable apparatus, a control mechanism which controls a communication state between the reservoir and the outside space, and a control unit which is formed to be detachable from the reservoir unit, the body-insertable apparatus assembling method characterized by including an opening process of taking off a leak-prevention tap inserted into the other end of the communicating channel, and an attaching process of attaching the control unit to the reservoir unit after leak-prevention tap is taken off.

INDUSTRIAL APPLICABILITY

As described above, the body-insertable apparatus according to the invention is useful for a medical observation apparatus which is introduced in a human body to observe a region to be tested. Particularly the invention is suitable for the realization of the body-insertable apparatus which can be miniaturized by devising the configuration of the line for communicating the reservoir and the outside space with each other, in the body-insertable apparatus which includes the predetermined reservoir and performs at least one of the release and suction of the fluid between the reservoir and the outside space.

The invention claimed is:

1. A body-insertable apparatus which is to be introduced in a subject to perform at least one of input and output of a predetermined fluid to and from the subject, the apparatus comprising:
   a reservoir in which the predetermined fluid is stored, the reservoir being placed at one end in a longitudinal direction of the body-insertable apparatus;
   a first communicating channel having an opening at a first end of the first communicating channel the first end of the first communicating channel being open to an inside of the reservoir, the first communicating channel being extended in the longitudinal direction of the body-insertable apparatus and surrounded by the reservoir;
   a second communicating channel having an opening at a first end of the second communicating channel, the first end of the second communicating channel being open to an outside space of the body-insertable apparatus, the second communicating channel being extended in a direction substantially parallel to the first communicating channel, and the second communicating channel partially running parallel to the first communicating channel;
   a communication adjusting mechanism with a sheet member which covers openings of second ends of the first and second communicating channels; and
   a control mechanism which controls a communication state between the first communicating channel and the second communicating channel by using the communication adjusting mechanism, the control mechanism being placed at another end in the longitudinal direction of the body-insertable apparatus.

2. The body-insertable apparatus according to claim 1, wherein the first communicating channel and the second communicating channel are formed by the same member.

3. The body-insertable apparatus according to claim 1, wherein the second communicating channel is substantially formed on a central axis in the longitudinal direction of the body-insertable apparatus.

4. The body-insertable apparatus according to claim 1, further comprising a weight member which is arranged near the opening of the second communicating channel, the opening of the second communicating channel being opened to the outside space of the body-insertable apparatus, the weight member acting so that the opening of the second communicating channel is opened downward in the subject.

5. The body-insertable apparatus according to claim 1, wherein the body-insertable apparatus is formed so that a center of gravity is located near the opening of the second communicating channel to the outside space of the body-insertable apparatus.

6. The body-insertable apparatus according to claim 1, wherein the opening at the second end of the first communicating channel and the opening at the second end of the second communicating channel are formed on the substantially same plane.

7. The body-insertable apparatus according to claim 1, wherein the first communicating channel and the second communicating channel are formed to be extended in directions substantially parallel to a longitudinal axis of the body-insertable apparatus at least near the second end of the first communicating channel and the second end of the second communicating channel.

8. The body-insertable apparatus according to claim 1, further comprising a volume changing member which changes a volume of the reservoir, wherein the volume changing member includes a piston forming a part of an outer wall portion of the reservoir, and an elastic member moving the piston.

9. The body-insertable apparatus according to claim 1, further comprising a volume changing member which changes a volume of the reservoir, wherein the volume changing member includes an elastic membrane.

10. The body-insertable apparatus according to claim 9, wherein the volume changing member, the reservoir, and the first communicating channel, and the second communicating channel form a reservoir unit, and
    the control mechanism, the communication adjusting mechanism, and the reservoir unit are sequentially arranged in the body-insertable apparatus.

11. The body-insertable apparatus according to claim 10, wherein the reservoir unit is detachable from other portions of the body-insertable apparatus.

12. The body-insertable apparatus according to claim 11, wherein
    the predetermined fluid outputted to the subject is previously stored in the reservoir, and the reservoir is formed such that a volume of a region in which the predetermined fluid is stored is changed according to the output of the predetermined fluid, and the reservoir unit further has an air space region whose volume is changed according to the volume change of the region, and the reservoir unit is formed such that at least the air space region is kept in a communicated state while the reservoir unit is mounted on the body-insertable apparatus.

13. The body-insertable apparatus according to claim 9, wherein the first communicating channel and the second communicating channel are extended in directions parallel to each other at least near the second end of each of the first communicating channel and the second communicating channel, the openings of the second ends of the first and second communicating channels are in the same plane, and the control mechanism controls the communication state between the first communicating channel and the second communicating channel by applying a variable pressing force to the sheet member in a direction parallel to the direction in which the first communicating channel and the second communicating channel are extended near the second ends and in the direction in which the sheet member abuts onto at least one of the openings at the second end of the first communicating channel and at the second end of the second communicating channel.

14. The body-insertable apparatus according to claim 13, wherein the communication adjusting mechanism further includes a pressing member which generates the pressing force applied by the sheet member.

15. The body-insertable apparatus according to claim 14, wherein the pressing member is a shape-variable member whose shape is changed by one of a temperature change and electrical current passage.

16. The body-insertable apparatus according to claim 15, wherein the pressing member further includes an elastic member which generates a pressing force, and when the shape-variable member is driven, the shape-variable member is deformed in the direction in which the pressing force generated by the elastic member is released.

17. The body-insertable apparatus according to claim 13, wherein a watertight member is provided between the sheet member and the openings of at least one of the first communicating channel and the second communicating channel.

18. The body-insertable apparatus according to claim 13, wherein the sheet member is a coupling member which couples the opening at the second end of the first communicating channel and the opening at the second end of the second communicating channel.

19. The body-insertable apparatus according to claim 13, wherein the sheet member is a shape-variable sheet whose shape is changed by one of a temperature change and an electrical current passage.

20. The body insertable apparatus of claim 1, wherein the longitudinal direction is a direction along a central axis of the body-insertable apparatus.

* * * * *